US012788850B2

(12) United States Patent
Do et al.

(10) Patent No.: US 12,788,850 B2
(45) Date of Patent: Nov. 10, 2026

(54) DRUG COATING FORMULATION FOR A SIROLIMUS COATED BALLOON CATHETER

(71) Applicant: C. R. Bard, Inc., Franklin Lakes, NJ (US)

(72) Inventors: Hiep Q Do, Chandler, AZ (US); Emily Goel, Phoenix, AZ (US); Cyal Lecy, Buffalo, MN (US); Logan Grace, Laveen, AZ (US); Jeffrey Wang, Phoenix, AZ (US); Dillon Mir, Chandler, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 97 days.

(21) Appl. No.: 18/696,272

(22) PCT Filed: Oct. 5, 2021

(86) PCT No.: PCT/US2021/053657
§ 371 (c)(1),
(2) Date: Mar. 27, 2024

(87) PCT Pub. No.: WO2023/059319
PCT Pub. Date: Apr. 13, 2023

(65) Prior Publication Data

US 2025/0041489 A1 Feb. 6, 2025

(51) Int. Cl.
*A61L 29/08* (2006.01)
*A61L 29/16* (2006.01)

(52) U.S. Cl.
CPC ............. *A61L 29/085* (2013.01); *A61L 29/16* (2013.01); *A61L 2300/416* (2013.01); *A61L 2300/606* (2013.01); *A61L 2300/622* (2013.01); *A61L 2300/802* (2013.01)

(58) Field of Classification Search
CPC .. A61L 29/085; A61L 29/16; A61L 2300/416; A61L 2300/606; A61L 2300/622; A61L 2300/802
See application file for complete search history.

(56) References Cited

U.S. PATENT DOCUMENTS

| | | | |
|---|---|---|---|
| 4,557,724 A | 12/1985 | Gregonis et al. | |
| 8,079,990 B2 | 12/2011 | Powley et al. | |
| 9,757,544 B2 | 9/2017 | Wang | |
| 2005/0037048 A1 | 2/2005 | Song | |
| 2006/0083768 A1 | 4/2006 | Labrecque et al. | |
| 2007/0083156 A1 | 4/2007 | Muto et al. | |
| 2009/0324684 A1 | 12/2009 | Atanasoska et al. | |
| 2011/0009953 A1 | 1/2011 | Luk et al. | |
| 2015/0024116 A1 | 1/2015 | Matson et al. | |
| 2016/0250387 A1 * | 9/2016 | Wang .................... | A61L 29/085 604/103.02 |
| 2018/0280581 A1 | 10/2018 | Mani et al. | |
| 2019/0358370 A1 | 11/2019 | Flanagan et al. | |
| 2020/0230390 A1 | 7/2020 | Powers et al. | |
| 2021/0154459 A1 | 5/2021 | Wiley et al. | |
| 2021/0213267 A1 | 7/2021 | DeMeritt | |
| 2021/0259976 A1 | 8/2021 | Wang et al. | |
| 2024/0382656 A1 | 11/2024 | Wang et al. | |

FOREIGN PATENT DOCUMENTS

| | | |
|---|---|---|
| EP | 2996735 B1 | 3/2019 |
| WO | 2005037338 A1 | 4/2005 |
| WO | 2014172569 A2 | 10/2014 |
| WO | 2020081455 A1 | 4/2020 |
| WO | 2023059318 A1 | 4/2023 |
| WO | 2023059319 A1 | 4/2023 |
| WO | 2023129132 A1 | 7/2023 |
| WO | 2024035435 A1 | 2/2024 |

OTHER PUBLICATIONS

PCT/US2021/053656 filed Oct. 5, 2021 International Preliminary Report on Patentability dated Apr. 9, 2024.

PCT/US2021/053656 filed Oct. 5, 2021 International Search Report and Written Opinion dated Jul. 7, 2022.

S. D. Lokeshwar et al., "A Surgeon's Guide to the Various Antibiotic Dips Available During Penile Prosthesis Implantation" SpringerLink, PubMed, Affiliations PMID: 30701340 DOI: 10.1007/s11934-019-0874-8. Jan. 30, 2019;20(2):11.

PCT/US2022/074825 filed Aug. 11, 2022 International Search Report and Written Opinion dated Mar. 24, 2023.

PCT/US2021/065323 filed Dec. 28, 2021, International Search Report and Written Opinion dated Aug. 25, 2022.

Fredenberg, Susanne, et al. "The mechanisms of drug release in poly (lactic-co-glycolic acid)-based drug delivery systems—A review." International Journal of Pharmaceutics 415.1-2 (2011): 34-52.

Min, Nam Gi, Tae Min Choi, and Shin-Hyun Kim. "Bicolored Janus Microparticles Created by Phase Separation in Emulsion Drops." Macromolecular Chemistry and Physics 218.2 (2017): 1600265.

PCT/US2021/053657 filed Oct. 5, 2021, International Search Report and Written Opinion dated Jun. 27, 2022.

U.S. Appl. No. 18/696,308, filed Mar. 27, 2024 Restriction Requirement dated Feb. 19, 2026.

Jin Yoo and You-Yeon Won; "Phenomenology of the Initial Burst Release of Drugs from PLGA Microparticles" (ACS Biomater. Sci. Eng. 2020, 6, 6053-6062) (Year: 2020).

U.S. Appl. No. 18/696,308, filed Mar. 27, 2024 Non-Final Office Action dated May 28, 2026.

* cited by examiner

*Primary Examiner* — Robert A Wax
*Assistant Examiner* — Quanglong N Truong
(74) *Attorney, Agent, or Firm* — Rutan & Tucker LLP

(57) ABSTRACT

The present disclosure relates to formulations for coating a balloon of a balloon catheter, the formulations including one or more groups of microparticles that include a therapeutic agent. In some aspects, the microparticles are polymer microparticles with the therapeutic dispersed therein or crystalline microparticles of the therapeutic agent. In some aspects, the formulations further include an antioxidant and/or an excipient.

23 Claims, 13 Drawing Sheets

(DCM)

(ethyl acetate

DRUG COATING FORMULATION FOR A SIROLIMUS COATED BALLOON CATHETER

PRIORITY

This application is a U.S. national stage application of International Application No. PCT/US2021/053657, filed Oct. 5, 2021, which is incorporated by reference in its entirety into this application.

TECHNICAL FIELD

The present specification generally relates to formulations for the delivery of sirolimus from a balloon of a balloon catheter.

BACKGROUND

The deployment of a medical device within a subject provides an opportunity to provide a therapeutic thereon to achieve localized drug-delivery. The combination of drug and device products offer the synergy between the mechanical function of the device itself and the effects from localized administration of an active pharmaceutical agent or drug. A drug coated balloon catheter is one example of one such combination devices. With a percutaneous transluminal angioplasty (PTA) balloon catheter, the balloon is coated with a drug coating containing an active pharmaceutical agent and excipients. When an arterial vessel is dilated by the balloon, drug coating on the balloon is pressed against the vessel wall to deliver the active pharmaceutical agent. Excipients in the drug coating are used to facilitate the rapid release of the drug off the balloon and the transfer thereof to the blood vessel tissues. Thus, excipients can play a key role in drug coated balloon catheter design.

To date, drug coated balloon catheters have concentrated on delivery of paclitaxel as an active pharmaceutical ingredient. Paclitaxel, however, can exert cytotoxic effects and there is therefore a need for formulations of other active agents that offer local beneficial effects with a lower cytotoxic potential. Sirolimus, or rapamycin, as well as related “limus” compounds such as tacrolimus, biolimus (biolimus A9), everolimus, zotarolimus, and pimecrolimus, is a cytostatic drug that is currently pursued as an alternative to paclitaxel due to the beneficial effect of inhibiting cell proliferation rather than causing cell death. However, sirolimus degrades rapidly in solution, in coating, and during storage making their presence in a drug coating challenging. Currently Concept Medical’s MagicTouch™ DCB seeks to utilize phospholipids to deliver sirolimus. However, while phospholipids are potentially of use or cross a cell’s membrane, the phospholipid mechanism does not prevent wash-off from the surface of the balloon, prevent hydrolysis during storage, or provide an extended release profile to sustain any cytostatic activity. Similarly, Clever et al. (Circulation: Cardiovascular Interventions, 2016; 9(4):e003543) report that deposition of crystalline sirolimus on the surface of a balloon can extend the half-life to four weeks as compared to amorphous sirolimus, yet identifies that sirolimus stents requires several weeks to produce a measurable effect. Accordingly, there is a need for formulating sirolimus for a drug coating on a balloon that protects sirolimus from the issues of wash-off and/or hydrolysis and promotes rapid transfer and uptake to allow sirolimus to exert the desired effect.

SUMMARY

The present disclosure concerns balloon catheters with a coating on an exterior surface thereof, the coating including one or more formulations of sirolimus and/or other limus compounds. In aspects, the present disclosure also concerns formulations with sirolimus, to provide a drug coating for a balloon catheter. The drug coating comprises of sirolimus and PLGA microparticles, and sodium docusate, petrolatum, or sodium docusate and petrolatum. The sirolimus/PLGA microparticles comprise of two sizes (~10 μm and ~35 μm). The smaller size microparticles provide initial burst of drug releasing and the larger size microparticles provide sustained drug releasing.

A first aspect of the present disclosure, either alone or in combination with any other aspects herein, concerns a formulation for a balloon of a balloon catheter, comprising: a first group of polymer microparticles, comprised of poly (lactic-co-glycolic acid) (PLGA) and a therapeutic agent loaded therein, wherein the therapeutic agent is a limus drug and is of 10 to 50% w/w; and an excipient, wherein the excipient is sodium docusate, petrolatum, or sodium docusate and petrolatum.

A second aspect of the present disclosure, either alone or in combination with any other aspects herein, concerns the formulation of the first aspect, wherein the polymer microparticles are smooth with even distribution of the therapeutic agent.

A third aspect of the present disclosure, either alone or in combination with any other aspects herein, concerns the formulation of the first aspect, wherein the polymer microparticles are contoured with clustered distribution of the therapeutic agent.

A fourth aspect of the present disclosure, either alone or in combination with any other aspects herein, concerns the formulation the second or third aspect, further comprising an antioxidant, wherein the antioxidant is butylated hydroxytoluene (BHT). BHT may be present at an amount of about 0.01 to 10% w/w.

A fifth aspect of the present disclosure, either alone or in combination with any other aspects herein, concerns the formulation of the first or third aspect, wherein the therapeutic agent is sirolimus.

A sixth aspect of the present disclosure, either alone or in combination with any other aspects herein, concerns the formulation of claim the first or third aspect, wherein the therapeutic agent is sirolimus and sirolimus is loaded in the polymer microparticle at 40% w/w.

A seventh aspect of the present disclosure, either alone or in combination with any other aspects herein, concerns the formulation of the sixth aspect, wherein the PLGA is of 75:25 of lactide to glycolide.

A eighth aspect of the present disclosure, either alone or in combination with any other aspects herein, concerns the formulation of the seventh aspect, further comprising a second group of the polymer microparticles, wherein the second group is of an average size that is of 20 μm to 30 μm larger than the first group.

A ninth aspect of the present disclosure, either alone or in combination with any other aspects herein, concerns the formulation of the eighth aspect, wherein the first group’s average size is 10 μm.

A tenth aspect of the present disclosure, either alone or in combination with any other aspects herein, concerns the formulation of the ninth aspect, wherein the second group’s average size is 30 μm.

An eleventh aspect of the present disclosure, either alone or in combination with any other aspects herein, concerns the formulation of the ninth aspect, wherein the second group's average size is 35 μm.

A twelfth aspect of the present disclosure, either alone or in combination with any other aspects herein, concerns the formulation of the ninth aspect, wherein the second group's average size is 40 μm.

A thirteenth aspect of the present disclosure, either alone or in combination with any other aspects herein, concerns a balloon catheter comprising a balloon with the formulation of the first aspect coated on at least a portion of an exterior surface thereof.

A fourteenth aspect of the present disclosure, either alone or in combination with any other aspects herein, concerns a formulation for a balloon of a balloon catheter, comprising: a first group and a second group of polymer microparticles, each group comprised of poly(lactic-co-glycolic acid) (PLGA) and a therapeutic agent loaded therein, wherein the therapeutic agent is a limus drug and is of 10 to 50% w/w of the polymer microparticles; and an excipient, wherein the excipient is sodium docusate, petrolatum, or sodium docusate and petrolatum, wherein the second group of polymer microparticles is of an average size that is 18-33 μm larger than the first group.

A fifteenth aspect of the present disclosure, either alone or in combination with any other aspects herein, concerns the formulation of the fourteenth aspect, wherein the polymer microparticles are smooth with an even distribution of the therapeutic agent therein.

A sixteenth aspect of the present disclosure, either alone or in combination with any other aspects herein, concerns the formulation of the fourteenth aspect, wherein the polymer microparticles are contoured with a clustered distribution of the therapeutic agent therein.

A seventeenth aspect of the present disclosure, either alone or in combination with any other aspects herein, concerns the formulation of the fifteenth or sixteenth aspect, further comprising an antioxidant, wherein the antioxidant is butylated hydroxytoluene (BHT).

An eighteenth aspect of the present disclosure, either alone or in combination with any other aspects herein, concerns the formulation of the fourteenth to seventeenth aspects, wherein the therapeutic agent is sirolimus.

A nineteenth aspect of the present disclosure, either alone or in combination with any other aspects herein, concerns the formulation of the eighteenth aspect, wherein sirolimus is loaded in the polymer microparticle at 40% w/w.

A twentieth aspect of the present disclosure, either alone or in combination with any other aspects herein, concerns the formulation of the nineteenth aspect, wherein the PLGA is of 75:25 of lactide to glycolide.

A twenty-first aspect of the present disclosure, either alone or in combination with any other aspects herein, concerns the formulation of the twentieth aspect, wherein the first group's average size is 10 μm.

A twenty-second aspect of the present disclosure, either alone or in combination with any other aspects herein, concerns the formulation of the twentieth aspect, wherein the second group's average size is 30 μm.

A twenty-third aspect of the present disclosure, either alone or in combination with any other aspects herein, concerns the formulation of the twentieth aspect, wherein the second group's average size is 35 μm.

A twenty-fourth aspect of the present disclosure, either alone or in combination with any other aspects herein, concerns the formulation of the twentieth aspect, wherein the second group's average size is 40 μm.

A twenty-fifth aspect of the present disclosure, either alone or in combination with any other aspects herein, concerns a balloon catheter comprising a balloon with the formulation of the fourteenth aspect coated on at least a portion of an exterior surface thereof.

A twenty-sixth aspect of the present disclosure, either alone or in combination with any other aspects herein, concerns a formulation for a balloon of a balloon catheter, comprising: a first group and a second group of uniformly sized PLGA-EtOAc sirolimus BHT polymer microparticles; and sodium docusate, wherein the first group is of an average size of 10 μm±10% and the second group of uniformly sized polymer microparticles is of an average size that is of 20 μm to 30 μm larger than the first group and further wherein sirolimus is 28.4% w/w of the formulation, PLGA-EtOAc is 42.6% w/w of the formulation and sodium docusate is 29% w/w of the formulation.

A twenty-seventh aspect of the present disclosure, either alone or in combination with any other aspects herein, concerns the formulation of the twenty-sixth aspect, wherein the PLGA is of 75:25 of lactide to glycolide.

A twenty-eighth aspect of the present disclosure, either alone or in combination with any other aspects herein, concerns the formulation of the twenty-sixth aspect, wherein the second group's average size is 30 μm.

A twenty-ninth aspect of the present disclosure, either alone or in combination with any other aspects herein, concerns the formulation of the twenty-sixth aspect, wherein the second group's average size is 35 μm.

A thirtieth aspect of the present disclosure, either alone or in combination with any other aspects herein, concerns the formulation of the twenty-sixth aspect, wherein the second group's uniform size is 40 μm.

A thirty-first aspect of the present disclosure, either alone or in combination with any other aspects herein, concerns a balloon catheter comprising a balloon with the formulation of the twenty-sixth aspect coated on at least a portion of an exterior surface thereof.

A thirty-second aspect of the present disclosure, either alone or in combination with any other aspects herein, concerns a formulation for a balloon of a balloon catheter, comprising: a first group of sirolimus crystalline microparticles; and a hydrophobic carrier, an excipient, or both a hydrophobic carrier and an excipient.

A thirty-third aspect of the present disclosure, either alone or in combination with any other aspects herein, concerns the formulation of the thirty-second aspect, wherein the hydrophobic carrier comprises a bioabsorbable hydrophobic polymer with a glass transition temperature of 37° C. or lower.

A thirty-fourth aspect of the present disclosure, either alone or in combination with any other aspects herein, concerns the formulation of the thirty-second aspect, wherein the hydrophobic carrier is petrolatum, a semi-synthetic glyceride, lecithin, or a combination thereof.

A thirty-fifth aspect of the present disclosure, either alone or in combination with any other aspects herein, concerns the formulation of the thirty-second aspect, wherein the excipient is sodium docusate.

A thirty-sixth aspect of the present disclosure, either alone or in combination with any other aspects herein, concerns a balloon catheter comprising a balloon with a formulation coated on at least a portion of an exterior surface thereof, wherein the formulation comprises: a first group and a second group of PLGA-EtOAc sirolimus BHT polymer microparticles; and sodium docusate, wherein the first group is of an average size of 10 μm and the second group is of an average that is of 20 μm to 30 μm larger.

A thirty-seventh aspect of the present disclosure, either alone or in combination with any other aspects herein, concerns the balloon catheter of the thirty-sixth, wherein sirolimus is of 28 to 29% w/w of the formulation.

A thirty-eighth aspect of the present disclosure, either alone or in combination with any other aspects herein, concerns the balloon catheter of the thirty-sixth or thirty-seventh aspect, wherein PLGA-EtOAc is of about 42-43% w/w of the formulation.

A thirty-ninth aspect of the present disclosure, either alone or in combination with any other aspects herein, concerns the balloon catheter of the thirty-sixth or thirty-eighth aspect, wherein sodium docusate is of about 28-30% w/w of the formulation.

A fortieth aspect of the present disclosure, either alone or in combination with any other aspects herein, concerns the balloon catheter of thirty-sixth or thirty-ninth aspect, further comprising an excipient layer underlying the formulation coated on the portion of the exterior surface of the balloon.

A forty-first aspect of the present disclosure, either alone or in combination with any other aspects herein, concerns the balloon catheter of the fortieth aspect, wherein the excipient is a surfactant, an antioxidant or a combination thereof.

A forty-second aspect of the present disclosure, either alone or in combination with any other aspects herein, concerns a method for coating a balloon of a balloon catheter comprising: preparing a coating slurry solution comprising a polymer microparticle of poly(lactic-co-glycolic acid) (PLGA) with a therapeutic agent loaded therein, a solvent, and an excipient; agitating the coating slurry solution; and applying the coating slurry solution to at least a portion of an exterior surface of the balloon in a unitary direction along the length of the balloon.

A forty-third aspect of the present disclosure, either alone or in combination with any other aspects herein, concerns the method of the forty-second aspect, wherein the coating slurry solution is agitated in a syringe with a stirrer in a barrel therein.

A forty-fourth aspect of the present disclosure, either alone or in combination with any other aspects herein, concerns the method of the forty-second aspect, wherein the coating slurry solution is agitated by stirring and then drawn into a barrel of a pipette.

A forty-fifth aspect of the present disclosure, either alone or in combination with any other aspects herein, concerns the method of the forty-fourth aspect, wherein the pipette is primed once with the coating slurry solution.

A forty-sixth aspect of the present disclosure, either alone or in combination with any other aspects herein, concerns the method of the forty-fourth aspect, wherein the pipette is disposed of after a single application of the coating slurry solution to the balloon.

A forty-seventh aspect of the present disclosure, either alone or in combination with any other aspects herein, concerns the method of the forty-third or forty-fourth aspect, wherein the coating slurry is applied to the balloon by dispensing the coating slurry solution through a tip operably connected to the barrel, wherein the dispensing is at a constant rate, the tip is maintained at an angle, and the tip moves along the length of the balloon at a constant rate.

A forty-eighth aspect of the present disclosure, either alone or in combination with any other aspects herein, concerns the method of the forty-seventh aspect, wherein the tip is at an angle that is 45 degrees, horizontal or vertical to the length of the balloon.

A forty-ninth aspect of the present disclosure, either alone or in combination with any other aspects herein, concerns the method of the forty-seventh aspect, wherein the coating slurry solution is dispensed at a rate of about 3 to about 100 μL/s.

BRIEF DESCRIPTION OF THE DRAWINGS

FIG. 1 depicts sirolimus loaded microspheres manufactured with dichloromethane (DCM) and ethyl acetate.

FIG. 8 shows the effects of various parameters on coating in an automated process.

DESCRIPTION

Figure 1A:
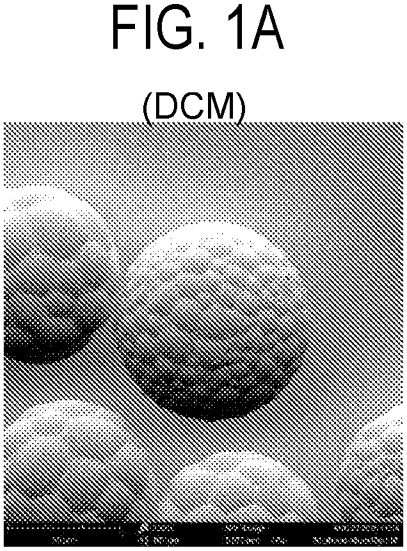
FIG. 1A shows a scanning electron microscopy (SEM) image of dichloromethane formed microparticles.

The present disclosure concerns balloon catheters, systems and methods for providing eluted limus drugs to the interior of a vasculature vessel wall. In some aspects, the present disclosure concerns formulations of microparticles or of groups of two or more microparticles that can provide limus drugs to the inner surface and/or internal tissue of a vessel wall of the vasculature of a subject.

In some aspects, the present disclosure concerns a coating layer or coating layers provided to the outer surface of a balloon catheter. In certain aspects, the balloon catheter is for improving and/or treating and/or repairing the vasculature of a subject, such as improving and/or treating and/or repairing the circulatory system flow in a subject. In some aspects, the balloon catheter is for insertion and/or implantation within a vessel of the vasculature or circulatory system of a subject, such as a blood vessel. In some aspects, the present disclosure concerns providing the balloon catheter to a subject. In some aspects, the balloon catheter is provided to the subject to treat or alleviate vascular stenosis. In some aspects, the balloon catheter is provided to treat and/or alleviate non-vascular stenosis and strictures, such as chronic sinusitis, asthma, chronic pulmonary obstruction, urethra stricture, bladder-neck stricture, and/or intestinal restructure. In some aspects, the present disclosure concerns coating layer(s) that provide for prolonged storage of a balloon catheter. In some aspect, the present disclosure concerns providing sirolimus in a formulation that can better protect against degradation during process such as sterilization and/or storage. In some aspects, loading and/or embedding sirolimus in a polymer microparticle can provide better protection against degradation during sterilization of the balloon catheter and/or the storage thereof.

In some aspects, the present disclosure concerns a formulation coated on the outer surface of a balloon catheter or a coating layer of a formulation. In some aspects, the formulation is coated or applied to the outer surface of the balloon of a balloon catheter to allow and/or provide contact between the coated formulation and the inner walls of vasculature vessel or the walls defining a lumen. As identified herein, the balloon catheters are for temporary placement within a vessel's lumen of the vasculature or circulatory system of a subject. By application of a formulation to the outer surface of the balloon of the balloon catheter, the formulation is able to come into contact with the inner surface of a vessel or lumen wall at one or more points. Those skilled in the art will appreciate that as the balloon can expand radially with respect to the cross-sectional circular nature of the vessels of a subject's circulatory system, the balloon will be able to press evenly into the vessel walls. Accordingly, in some aspects, one or more formulation(s) of the present disclosure may come into contact with the vessel wall when the balloon of the balloon catheter is expanded within the vessel of the subject.

Therapeutic Agent

In some aspects, the present disclosure concerns formulations comprised of microparticles. In some aspects, the microparticles include a therapeutic agent. In some aspects, the microparticles are of a crystalline therapeutic agent. In other aspects, the microparticles are of a polymer with a therapeutic agent embedded therein. In some aspects, the therapeutic agent is a limus drug, such as sirolimus. It will be appreciated, however, that while the examples herein demonstrate effective uptake of sirolimus, the active agent on the exterior surface of the balloon does not need to be limited to such.

In some aspects, the present disclosure concerns coatings of formulations of microparticles that include limus drugs, including sirolimus, biolimus, everolimus, zotarolimus, and pimecrolimus. In some aspects, the formulation is of microparticles of one or more crystalline limus drugs coated on the exterior surface of the balloon of a balloon catheter. In some aspects, the crystalline limus drugs are of groupings of one or more different sizes. In some aspects, the crystalline drugs are of two or more groups of differing sizes. In other aspects, the formulation is of microparticles of a polymer with a limus drug suspended therein. In some aspects, the formulation is of one or more groups of sizes of microparticle of polymer with a limus drug suspended therein. In other aspects, the formulation is of two of more groups of sizes of microparticles of polymer with a limus drug suspended therein.

In some aspects, the present disclosure concerns limus drugs and derivatives and analogs thereof, such as derivative and/or analogs of sirolimus. In other aspects, the present disclosure generally concerns a therapeutic agent or drug and derivatives and/or analogs thereof. As used herein, "derivative" refers to a chemically or biologically modified version of a chemical compound that is structurally similar to a parent compound and (actually or theoretically) derivable from that parent compound (for example, dexamethasone). A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). The term "derivative" also includes conjugates, and prodrugs of a parent compound (i.e., chemically modified derivatives which can be converted into the original compound under physiological conditions). For example, the prodrug may be an inactive form of an active agent. Under physiological conditions, the prodrug may be converted into the active form of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs is found, for example, in Fleisher et al., Advanced Drug Delivery Reviews 19 (1996) 115; Design of Prodrugs, H. Bundgaard (ed.), Elsevier, 1985; or H. Bundgaard, Drugs of the Future 16 (1991) 443. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form alkali metal salts or alkaline earth metal salts (e.g., sodium salts, potassium salts, magnesium salts and calcium salts, as well as salts with physiologically tolerable quaternary ammonium ions and acid addition salts with ammonia and physiologically tolerable organic amines such as triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds which simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, “analog” or “analogue” may refer to a chemical compound that is structurally similar to another but differs slightly in composition (as in the replacement of one atom by an atom of a different element or in the presence of a particular functional group), but may or may not be derivable from the parent compound. A “derivative” differs from an “analog” or “analogue” in that a parent compound may be the starting material to generate a “derivative,” whereas the parent compound may not necessarily be used as the starting material to generate an “analog.”

It will also be appreciated that the formulations and microparticles as disclosed herein need not be limited to a single therapeutic agent, but may include one or more additional therapeutic agent(s) or drug(s) and/or derivatives and/or analogs thereof. Other drugs that may be useful in the present disclosure include, without limitation, glucocorticoids (e.g., cortisol, betamethasone), hirudin, angiopeptin, acetylsalicyclic acid, NSAIDs (non-steroidal anti-inflammatory drugs), growth factors, antisense agents, anti-cancer agents, anti-proliferative agents, oligonucleotides, and, more generally, anti-platelet agents, anti-coagulant agents, anti-mitotic agents, antioxidants, anti-metabolite agents, anti-chemotactic, and anti-inflammatory agents. Also useful in aspects of the present disclosure are polynucleotides, anti-sense, RNAi, or siRNA, for example, that inhibit inflammation and/or smooth muscle cell or fibroblast proliferation, contractility, or mobility. Anti-platelet agents can include drugs such as aspirin and dipyridamole. Aspirin is classified as an analgesic, antipyretic, anti-inflammatory and anti-platelet drug. Dipyridamole is a drug similar to aspirin in that it has anti-platelet characteristics. Dipyridamole is also classified as a coronary vasodilator. Anti-coagulant agents for use in aspects of the present disclosure can include drugs such as heparin, protamine, hirudin and tick anticoagulant protein. Anti-oxidant agents can include probucol. Anti-proliferative agents can include drugs such as paclitaxel, amlodipine and doxazosin. Anti-mitotic agents and anti-metabolite agents that can be used in aspects of the present disclosure include drugs such as methotrexate, azathioprine, vincristine, adriamycin, and mutamycin. Antibiotic agents for use in aspects of the present disclosure include penicillin, cefoxitin, oxacillin, tobramycin, and gentamicin. Suitable antioxidants for use in aspects of the present disclosure include probucol. Additionally, genes or nucleic acids, or portions thereof can be used as the therapeutic agent in aspects of the present disclosure. Photosensitizing agents for photodynamic or radiation therapy, including various porphyrin compounds such as porfimer, for example, are also useful as drugs in aspects of the present disclosure.

Crystalline Microparticle Formulations

In some aspects, the formulation is of microparticles of one or more crystalline limus drugs applied to the exterior surface of the balloon. In certain aspects, the formulation is of microparticles crystalline sirolimus applied to the exterior surface of a balloon. In some aspects, the microparticles are of a crystalline limus drug of one average size, typically measured as a cross-sectional width of a microparticle. As used herein, “size” with respect to microparticles, either crystalline microparticles or polymer microparticles refers to a diameter or cross-sectional width of the microparticle. As also used herein, an average size may refer to an isolated or previously isolated collection of crystalline microparticles that have been selected for a particular diameter or cross-sectional width, such that the collection of crystalline microparticles are of the desired selection size (e.g., average and/or D50 or $50^{th}$ percentile distribution)±10 μm or less or ±20% of the selected size or within one or two standard deviations thereof. In some aspects, the formulation includes at least two different sized populations or groups of crystalline microparticles to provide a mixture of relatively larger crystalline microparticles and of relatively smaller crystalline microparticles. It will be appreciated that the number of populations of crystalline microparticles need not be limited, such that three, four, five, six, seven, eight, nine, ten, and so on can be utilized. It will be understood, however, that an objective of a short burst and a prolonged burst of drug release as discussed herein can be achieved with as few as two populations of crystalline microparticles.

In some aspects, the formulations of the present disclosure concern application of a population or group of sized crystalline microparticles to the exterior surface of a balloon. In some aspects, the sizing is of an average size or a distribution size (D50) or a uniform size. A distribution size may include a value representing the percentage of particles that are below that value, such as a D50 value represents a value at which 50% of particles are equal to or smaller than that value. In some aspects, the average size is the D50 value. D50 values can be determined through processes such as laser diffraction. A uniform size refers to each microparticle being of the same size or of a size within 20% of the selected or average size. In some aspects, the formulation may be of two or more populations of uniformly sized crystalline microparticles, where one population is of a smaller selected size than the other population. Crystalline microparticles can be obtained by grinding down limus drug crystals to desired particle sizes. Grinding can be achieved through devices such as jaw crushers, rotor mills, cutting and knife mills, disc mills, mortar grinders, and ball mills. The process for achieving crystalline microparticles can be through dry milling, wet milling and/or cryo-milling. Following the grinding, crystalline microparticles of a particular desired size can be achieved through size selection processes, such as meshing, sieving, weight selection, and filtration.

In some aspects, the formulation includes a hydrophobic carrier that aids in retaining the crystalline microparticles on the exterior surface of the balloon at room temperature and aids in transferring the crystalline microparticles to a vessel wall at the body temperature of the subject receiving the balloon catheter. In some aspects, the hydrophobic carrier may include, but is not limited to, hydrophobic polymers and/or hydrophobic small molecules that are bioabsorbable hydrophobic materials. In some aspects, the hydrophobic layer may be a mixture of two or more hydrophobic materials that are selected on the basis that they are biodegradable and/or bioabsorbed by the body over time. By way of example and not limitation, examples of bioabsorbable hydrophobic materials may include semi-synthetic glycerides (e.g. Suppocire AIML, AML, BML, BS2, BS2X, NBL, NAIS 10, CS2X), lecithin, hydrogenated coconut oil, coconut oil, mineral oil, cetyl alcohol, petrolatum, petroleum jelly, decanol, soft paraffin, tridecanol, dodecanol, long chain saturated fatty acids, long chain unsaturated fatty acids, fatty acid esters, fatty acid ethers, witepsol, solid lipids, methyl stearate, triglycerides, glyceryl monostearate, glyceryl palmitostearate, stearic acid, palmitic acid, decanoic acid, behenic acid, beeswax, carnauba wax, paraffin, fatty acid triglycerides, fatty acid alcohols or combinations thereof.

In some aspects, the bioabsorbable hydrophobic polymer and/or hydrophobic small molecule has a glass transition temperature of 37° C. or lower. By providing a hydrophobic carrier with a glass transition temperature that is below body temperature, the hydrophobic carrier can become tacky or sticky when the balloon catheter is placed in situ within a human subject. In some aspects, the body temperature of the tissue surrounding the balloon when placed and inflated in a subject warms the hydrophobic carrier to above the glass transition temperature, allowing the hydrophobic carrier to become sticky or tacky within the subject. The ability of the hydrophobic carrier to become tacky allows the coating to adhere or transfer from the outer surface of the balloon to the vessel wall. In some aspects, providing the crystalline microparticles within the hydrophobic carrier restricts exposure to water or the hemic environment or the aqueous environment of the subject's blood and as a result dug absorption by the vessel wall may be prolonged. In some aspects, prolonging the time course of uptake of the active agent can prevent or reduce incidences of restenosis.

In some aspects, the formulation for the coating includes a uniformly sized population of crystalline microparticles and a hydrophobic carrier, such as crystalline microparticles of a limus drug, such as sirolimus. In some aspects, the uniform population size is of 20 to 40 μm in width or diameter.

In some aspects, the formulation can be prepared by adding the hydrophobic carrier and the crystalline microparticles in an organic or hydrophobic solvent. In such a solvent, the crystalline microparticles does not dissolve, but the hydrophobic carrier does. The solution can then be applied to the exterior surface and as the solvent evaporates, the hydrophobic carrier emerges from the applied solution and retains the crystalline microparticles on the exterior surface of the balloon. In some aspects, the hydrophobic carrier is of petrolatum and the crystalline microparticles are of sirolimus.

In some aspects, the formulation includes crystalline microparticles as described herein and a hydrophobic carrier and/or an excipient. In some aspects, the hydrophobic carrier is of petrolatum, semi-synthetic glycerides, lecithin, or combinations thereof and the excipient is sodium docusate. In some aspects, the crystalline microparticles are of about 20 to about 90% w/w of the formulation and the hydrophobic carrier is of about 15 to about 90% w/w of the formulation and the excipient is of about 1 to about 60% w/w of the formulation. In some aspects, the excipient is of about 2, 5, 10, 15, 20, 25, 30, 35, 40, 45, 50, 55, or 60% w/w of the formulation. In some aspects, the excipient is of 1-45, 1-40, 1-35, 1-30, 1-25, 1-20, 5-50, 5-40, 5-30, 10-50, 10-40, or 20-50% w/w of the formulation. In some aspects, the crystalline microparticles are of 20, 25, 30, 35, 40, 45, 50, 55, 60, 65, 70, 75, 80, 85, or 90% w/w of the formulation. In some aspects, the polymer microparticles are of 20-90, 20-75, 20-70, 20-60, 50-90, 50-75, 50-70, 50-65, 50-60, 60-80, 60-75, or 60-70% w/w of the formulation. In some aspects, the hydrophobic carrier is of 15, 20, 25, 30, 35, 40, 45, 50, 55, 60, 65, 70, 75, 80, 85, or 90% w/w of the formulation. In some aspects the hydrophobic carrier is of 15-90, 15-80, 15-70, 15-60, 15-50, 15-40, 30-90, 30-80, 30, 70, 30-60, 50-90, 60-90, or 70-90% w/w of the formulation.

Polymer Microparticle Formulations

In other aspects of the present disclosure, the polymer microparticles of the present disclosure are of a polymer with an active drug suspended therein. In certain aspects, the polymer microparticles are of two or more differently sized populations of polymer with an active drug suspended therein. In some aspects, the microparticles are of bioabsorbable polymer microparticles with a limus drug embedded therein. In some aspects, the polymer microparticles are of bioabsorbable polymer microparticles with sirolimus embedded therein. In some aspects, a bioabsorbable polymer of the microparticle may include a polymer or linked or cross-linked network of one or more of glycolic acid and lactic acid or L-lactic acid, including polyglycolic acid and poly-L-lactic acid. In some aspects, a bioabsorbable polymer utilized for the microparticles may be a combination of polymers, such as a polymer network of a poly-glycolic acid (PGA) and a poly-L-lactic acid (PLLA). Other bioabsorbable polymers that can be utilized in combination or alone for the microparticles include polycaprolactone (PCL), poly-DL-lactic acid (PDLLA), poly(trimethylene carbonate) (PTMC), poly (ester amine)s (PEA), and poly(para-dioxanone) (PPDO), poly-2-hydroxy butyrate (PHB), and co-polymers with various ratios of these polymers. In some aspects, the bioabsorbable polymer may include, either alone or in combination with other bioabsorbable polymers, a polymer combination of lactic acid and glycolic acid: poly-lactic-co-glycolic acid (PLGA). Those skilled in the art will appreciate that PLGA can be of varying percentages of lactic acid and glycolic acid, wherein the higher the amount of lactide units, the longer the polymer can last in situ before degrading. Additional tunable properties with PLGA concern the molecular weight, such higher weights showing increased mechanical strength. In some aspects, more than one bioabsorbable polymer can be utilized for each polymer microparticle and/or various different therapeutic loaded polymer microparticles can be utilized to provide for a desired therapeutic release profile. In some aspects, the therapeutic dispersed in a polymer is prepared by emulsion evaporation, wherein the therapeutic agent and the polymer are mixed in a solvent such as dichloromethane or ethyl acetate and then formed as the solvent evaporates. Size of the microparticles can be controlled by processes such as microfluidic channel size or membrane emulsification. In some aspects, the polymer microparticles may be prepared with an antioxidant as set forth herein. In some aspects, the polymer microparticles are prepared with butylated hydroxytoluene (BHT).

In some aspects, the bioabsorbable polymer may be a polymer of appended units, such as appended with an amine, a carboxylic acid, a polyethylene glycol (PEG), or an amino acid. In some aspects, the bioabsorbable polymer is an appended PLGA.

In some aspects of the present disclosure, the solvent utilized in preparing the microparticles of a polymer with a therapeutic embedded therein will produce different polymer microparticles that differ in morphology, drug loading profile, and drug elution.

In some aspects, the present disclosure concerns formulations for preparing polymer microparticles. In some aspects, the formulation includes a solvent, an antioxidant, a polymer and a therapeutic agent. In some aspects, the solvent is of dichloromethane (DCM), ethyl acetate (EtOAc). In certain aspects, the formulation for the polymer microparticles includes DCM or EtOAc and PLGA, sirolimus, and BHT.

Figure 1B:
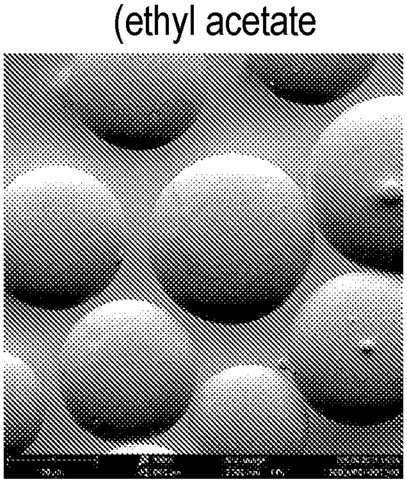
FIG. 1B shows a SEM image of ethyl acetate formed microparticles.
Figure 1C:
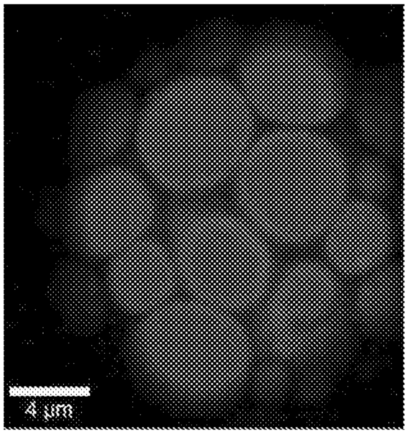
FIG. 1C shows a Raman spectroscopy image of sirolimus distribution in a DCM microparticle.

In some aspects, the present disclosure concerns contoured polymer microparticles. Contoured polymer microparticles refer to polymer microparticles obtainable by evaporating droplets of polymer-drug solvent from membrane emulsification and/or microfluidics, with solvents such as dichloromethane (DCM). As evidenced in FIG. 1A, scanning electron microscopy shows the surface of polymers formed with DCM to possess an uneven, contoured surface. Further, Raman spectroscopy imaging, FIG. 1C, shows that the active agent is embedded within the polymer microparticle in concentrated groups. In some aspects, the present disclosure concerns contoured microparticles of PLGA or PLGA-DCM microparticles. As referenced herein, PLGA-DCM refers to contoured polymer microparticles of PLGA that form when DCM is the solvent. PLGA-DCM also refers to an embedded drug therein being clustered as depicted in FIG. 1C.

Figure 1D:
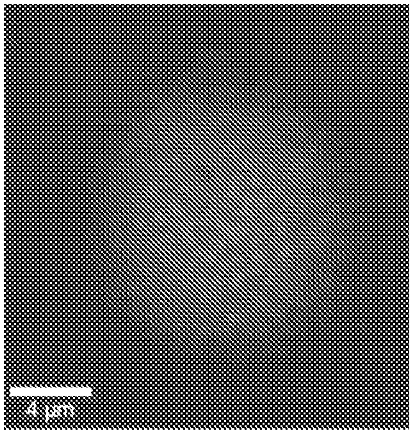
FIG. 1D shows a Raman spectroscopy image of sirolimus distribution in an ethyl acetate formed microparticle.

In some aspects, the present disclosure concerns smooth polymer microparticles. Smooth polymer microparticles refer to polymer microparticles obtainable by evaporating droplets of polymer-drug solvent from membrane emulsification and/or microfluidics, with solvents such as ethyl acetate (EtOAc). As evidenced in FIG. 1B, scanning electron microscopy shows the surface of polymers formed with ethyl acetate to possess even, smooth surfaces. Further, Raman spectroscopy imaging, FIG. 1D, shows that the active agent is embedded within the polymer microparticle in an even manner. In some aspects, the present disclosure concerns contoured polymer microparticles of PLGA or PLGA-EtOAc. As referenced herein, PLGA-EtOAc refers to smooth polymer microparticles of PLGA that form when EtOAc is the solvent. PLGA-EtOAc also refers to an even distribution of embedded drug throughout the microparticle as depicted in FIG. 1D.

In some aspects, the coating of the exterior surface is of a formulation of contoured polymer microparticles of a bioabsorbable polymer with a therapeutic agent embedded therein. As evidenced, the therapeutic agent will be embedded in concentrated clusters. In other aspects, the coating of the exterior surface is of a formulation of smooth polymer microparticles of a bioabsorbable polymer with a therapeutic agent embedded therein. As evidenced, the therapeutic agent will be embedded evenly throughout the polymer microparticle. In some aspects, the coating of the exterior surface is of a formulation of contoured polymer microparticles and smooth polymer microparticles, both with a therapeutic agent embedded therein. In some aspects, the therapeutic agent is a limus drug. In certain aspects, the therapeutic agent is sirolimus. The smooth polymer microparticles further provide a slower dissolution of embedded therapeutic than contoured polymer microparticles (see FIG. 2). In some aspects, the coating of the exterior surface is of a formulation of PLGA-EtOAc and/or PLGA-DCM, each being embedded or loaded with a limus drug. In some aspects, the coating of the exterior surface is of a formulation of PLGA-EtOAc and/or PLGA-DCM, each being embedded or loaded with sirolimus.

In other aspects of the present disclosure, the polymer microparticles are of a bioabsorbable polymer embedded with a therapeutic, the microparticle being of an average size or D50±a standard deviation, wherein the standard deviation is of about 10 μm or less, including about 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.0, 5.8, 5.7, 5.6, 5.5, 5.4, 5.3, 5.2, 5.1, 5.0 and less. In some aspects, the polymer microparticles may have average size of from 100 nm to 200 μm, including 0.2, 0.3, 0.4, 0.5, 0.6, 0.7, 0.8, 0.9, 1, 1, 2, 3, 4, 5, 6, 7, 8, 9, 10, 20, 30, 40, 50, 60, 70, 80, 90, 110, 120, 130, 140, 150, 160, 170, 180, and 190 μm. In some aspects, the average size may be of about 100 nm to about 300 μm. In some aspects, the average size or D50 may be of about 1 μm to about 300 μm, of about 1 μm to about 100 μm, of about 1 μm to about 50 μm, of about 1 μm to about 40 μm, of about 1 μm to about 30 μm, of about 10 μm to about 300 μm, of about 10 μm to about 100 μm, of about 10 μm to about, of about 10 μm to about 40 μm, or of about 10 μm to about 30 μm. "Size", with respect to microparticles, either crystalline microparticles or polymer microparticles, refers to a diameter or cross-sectional width of the microparticle. For example a 10 μm polymer microparticle has a diameter or cross-sectional width of 10 μm. In some aspects, the average size is the D50 value. D50 values can be determined through processes such as laser diffraction. In other aspects of the present disclosure, the polymer microparticles are of a bioabsorbable polymer embedded with a therapeutic, the microparticle being of a uniform size or of a narrow distribution of size, such that 95% of the polymer microparticles are within 20 percent or less of the average selected size. Providing the coating with a uniform or near uniform polymer microparticle size can allow for uniform dissolution of the embedded therapeutic. In some aspects, the polymer microparticles may have a uniform or narrow distribution size of from 100 nm to 200 μm (±20%), including 0.2, 0.3, 0.4, 0.5, 0.6, 0.7, 0.8, 0.9, 1, 1, 2, 3, 4, 5, 6, 7, 8, 9, 10, 20, 30, 40, 50, 60, 70, 80, 90, 110, 120, 130, 140, 150, 160, 170, 180, and 190 μm (all ±10%). In some aspects, the narrow distribution of particles may be of about 100 nm±20 nm to about 300 μm±60 μm. In some aspects, the narrow distribution of particles may be of about 1 μm±0.2 μm to about 300 μm±60 μm, of about 1 μm±0.2 μm to about 100 μm±20 μm, of about 1 μm±0.2 μm to about 50 μm±10 μm, of about 1 μm±0.2 μm to about 40 μm±8 μm, of about 1 μm±0.2 μm to about 30 μm±6 μm, of about 10 μm±2 μm to about 300 μm±60 μm, of about 10 μm±2 μm to about 100 μm±20 μm, of about 10 μm±2 μm to about 50 μm±10 μm, of about 10 μm±2 μm to about 40 μm±8 μm, or of about 10 μm±2 μm to about 30 μm±6 μm.

Figure 3:
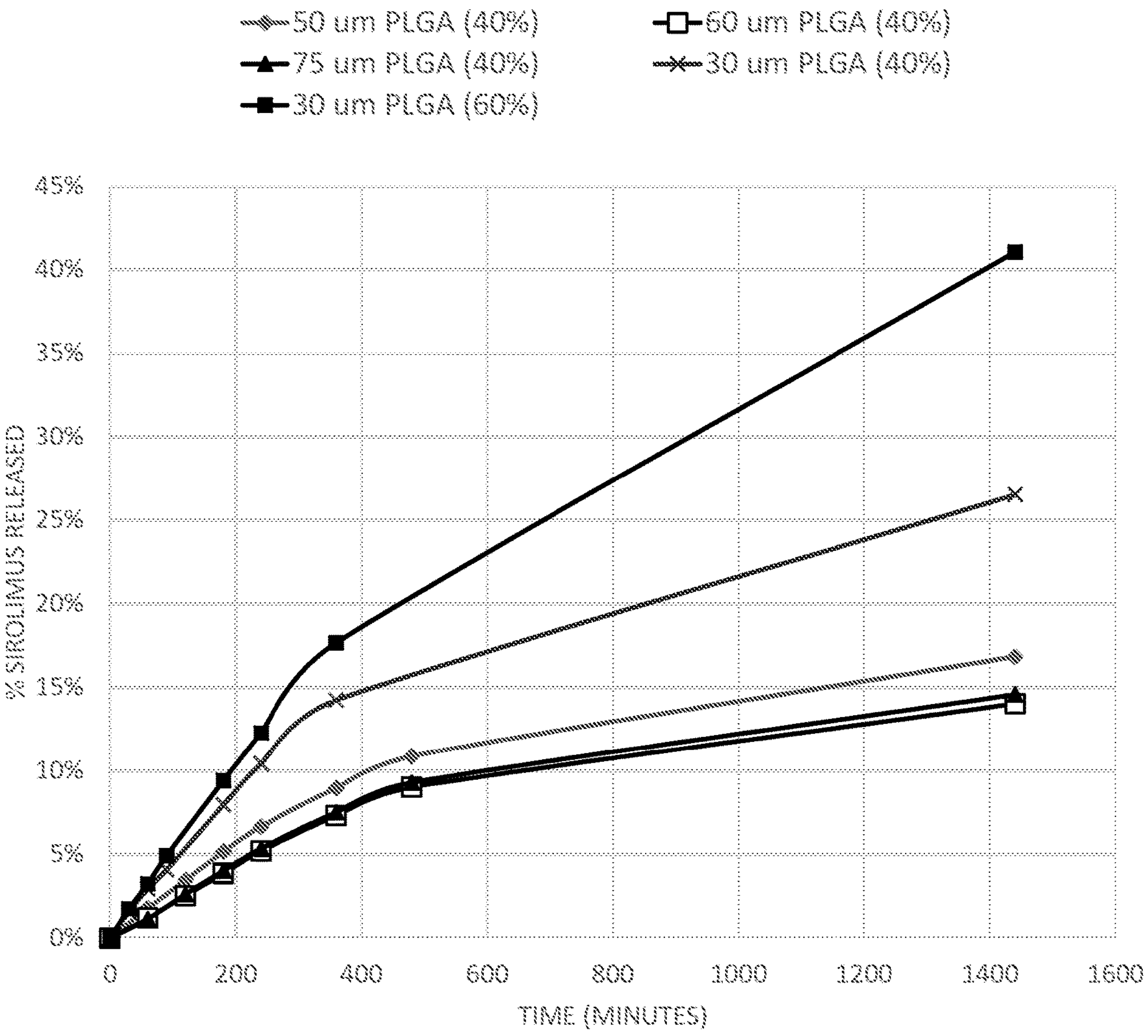
FIG. 3 depicts sirolimus PLGA microsphere elution of various particle sizes and different drug loading.

Selection of the size of polymer microparticle can depend on the desired rate of dissolution of the embedded therapeutic. Selection of a smaller polymer microparticle provides a more rapid rate of dissolution than a comparatively larger microparticle. For example, as depicted in FIG. 3, a 30 μm polymer microparticle of PLGA with 40% drug loading with sirolimus released sirolimus at a higher rate than a 50 μm polymer microparticle of PLGA with 40% drug loading with sirolimus.

Through techniques such as microfluidics and membrane emulsification, it is possible to control the size of polymer microparticle formed. For example, polymer microparticle size and size distribution can be controlled by the dispersing phase flow rate, the continuous phase flow rate, the microfluidic chip channel size, and the solid percentage in the dispersing phase. In evaporative emulsion, polymer microparticle size and size distribution can be controlled by the dispersing phase injection rate, the stirring rate in the continuous phase reservoir, the membrane pore size, and the solid percentage in the dispersing phase.

In some aspects, the polymer microparticle may be loaded or embedded with a pre-determined amount of therapeutic agent. By increasing the amount of therapeutic agent present in the solvent as the polymer microparticles are formed provides for a higher drug loading. As depicted, e.g., in FIG. 3, 60% loading of sirolimus in a 30 μm PLGA microparticle has a higher release of sirolimus than a 40% loading of sirolimus in a 30 μm PLGA microparticle. In some aspects, the polymer microparticle is loaded or embedded with a therapeutic such that the therapeutic is of from 5 to 75% by weight of the polymer microparticle (w/w), including 10, 15, 20, 25, 30, 35, 40, 45, 50, 55, 60, 65, and 70% by weight of the polymer microparticle. In some aspects, the polymer microparticle is of 10-70, 10-60, 10-50, 10-40, 10-30. 20-70, 20-60, 20-50, 20-40, 30-70, 30-60, 30-50, 35-45, or 40-50% w/w of the therapeutic. In some aspects, the present disclosure concerns polymer microparticles loaded or embedded with sirolimus, such that sirolimus is of 5 to 75% w/w of the polymer microparticle, including 10, 15, 20, 25, 30, 35, 40, 45, 50, 55, 60, 65, and 70% w/w of the polymer microparticle.

In some aspects, the choice of polymer and/or the concentration of polymer may provide for further variety in dissolution of the therapeutic agent. In some aspects, the polymer of the polymer microparticle may be of a 75:25 PLGA (75 LA/lactide to 25 GA/glycolide) at from 10-80% w/w of the polymer microparticle, including 15, 20, 25, 30, 35, 40, 45, 50, 55, 60, 65, 70, and 75% w/w of the polymer microparticle. In other aspects, the polymer microparticle is of another bioabsorbable polymer. As identified in FIG. 4, sirolimus can elute at a faster rate from PLA than from PLGA. In further aspects, the polymer microparticles can be prepared with one or more bioabsorbable polymers, such as PLGA and PLA, PLGA and PGA, PLGA and PLLA, PLGA and PCL, PLGA and PDLLA, PLGA and PTMC, PLGA and PEA, or PLGA and PPDO. In other aspects, the polymer microparticles may be of PLGA and one or more of PLA, PLLA, PGA, PDLLA, PCL, PTMC, PEA, and PPDO. In each instance, the polymer microparticle may be a DCM microparticle and/or an EtOAc microparticle.

In some aspects, the polymer microparticle is of PLGA loaded or embedded with a therapeutic. In some aspects, the therapeutic is a limus drug. In certain aspects, the therapeutic is sirolimus. In further aspects, the therapeutic is sirolimus loaded at 35-45% w/w of the polymer microparticle. In some aspects, the PLGA is PLGA-DCM. In other aspect, the PLGA is PLGA-EtOAc. In even further aspects, the polymer microparticle is a combination of PLGA-DCM and PLGA-EtOAc. In some aspects, the polymer microparticle is of 10, 20, 30, 40, or 50 μm in average size and is of PLGA loaded with sirolimus at 35-45% w/w of the polymer microparticle. In other aspects, the polymer microparticle features at least one other polymer in addition to PLGA, selected from PLA, PLLA, PGA, PDLLA, PCL, PTMC, PEA, PPDO, PHB, and combinations thereof.

In some aspects, the polymer microparticle can be tuned to meet a desired release profile. For example, the solvent utilized can provide for differences in release rates. The size of the polymer microparticle can provide for differences in release profile. The amount of therapeutic agent loaded or embedded within the polymer microparticle can provide for differences in release profile. The polymer composition can provide for differences in release rate. For example, a polymer microparticle of PLGA-EtOAc with sirolimus loaded 35-45% w/w of the polymer microparticle and an average size of 30 μm can be tuned by, e.g. (and not by way of limitation): reducing the average size to 10 μm to increase sirolimus release; switching to PLGA-DCM to increase sirolimus release; increasing sirolimus loading to increase sirolimus release; and, adding a faster degrading polymer such as PLA to increase sirolimus release.

In some aspects, the polymer microparticle is of a bioabsorbable polymer, a therapeutic agent, and an antioxidant. An antioxidant is a molecule capable of slowing or preventing the oxidation of other molecules. Oxidation reactions can produce free radicals and/or peroxides, which start chain reactions and may cause degradation of therapeutic agents. Antioxidants terminate these chain reactions by removing free radicals and inhibiting oxidation of the active agent by being oxidized themselves. Antioxidants are used as the one or more additional excipients in certain aspects to prevent or slow the oxidation of the therapeutic agents in the coatings for medical devices. Antioxidants are a type of free radical scavengers. The antioxidant may be used alone or in combination with other additional excipients in certain aspects and may prevent degradation of the active therapeutic agent during sterilization or storage prior to use. Some representative examples of antioxidants that may be used in the drug coatings of the present disclosure include, without limitation, oligomeric or polymeric proanthocyanidins, polyphenols, polyphosphates, polyazomethine, high sulfate agar oligomers, chitooligosaccharides obtained by partial chitosan hydrolysis, polyfunctional oligomeric thioethers with sterically hindered phenols, hindered amines such as, without limitation, p-phenylene diamine, trimethyl dihydroquinolones, and alkylated diphenyl amines, substituted phenolic compounds with one or more bulky functional groups (hindered phenols) such as tertiary butyl, arylamines, phosphites, hydroxylamines, and benzofuranones. Also, aromatic amines such as p-phenylenediamine, diphenylamine, and N,N'disubstituted p-phenylene diamines may be utilized as free radical scavengers. Other examples include, without limitation, butylated hydroxytoluene ("BHT"), butylated hydroxyanisole ("BHA"), L-ascorbate (Vitamin C), Vitamin E, herbal rosemary, sage extracts, glutathione, resveratrol, ethoxyquin, rosmanol, isorosmanol, rosmaridiphenol, propyl gallate, gallic acid, caffeic acid, p-coumeric acid, p-hydroxy benzoic acid, astaxanthin, ferulic acid, dehydrozingerone, chlorogenic acid, ellagic acid, propyl paraben, sinapic acid, daidzin, glycitin, genistin, daidzein, glycitein, genistein, isoflavones, and tertbutylhydroquinone. Examples of some phosphites include di(stearyl)pentaerythritol diphosphite, tris(2,4-di-tert.butyl phenyl)phosphite, dilauryl thiodipropionate and bis(2,4-di-tert.butyl phenyl)pentaerythritol diphosphite. Some examples, without limitation, of hindered phenols include octadecyl-3,5,di-tert.butyl-4-hydroxy cinnamate, tetrakis-methylene-3-(3',5'-di-tert-.butyl-4-hydroxyphenyl)propionate methane 2,5-di-tert-butylhydroquinone, ionol, pyrogallol, retinol, and octadecyl-3-(3,5-di-tert.butyl-4-hydroxyphenyl)propionate. An antioxidant may include glutathione, lipoic acid, melatonin, tocopherols, tocotrienols, thiols, beta-carotene, retinoic acid, cryptoxanthin, 2,6-di-tert-butylphenol, propyl gallate, catechin, catechin gallate, and quercetin. In certain aspects, the antioxidant is butylated hydroxytoluene (BHT). In some aspects, the antioxidant is of about 0.01 to about 10% w/w of the polymer microparticle, including about 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, and 9 5% w/w. In some aspects, the antioxidant is of 0.01 to 10, 0.1 to 5, 0.01 to 1, 0.1 to 10, 0.1 to 5, 0.1 to 1, 1 to 10, 1 to 5, 1 to 3, 2 to 10, 2 to 5, 2-3, 3 to 10, or 3 to 5% w/w of the polymer microparticle. In certain aspects, the antioxidant is of about 0.01% w/w of the polymer microparticle. In some aspects, the antioxidant is 3% or about 3% w/w of the polymer microparticle or a formulation for the formation thereof. In certain aspects, the antioxidant is BHT.

In some aspects, the polymer microparticle is of PLGA loaded or embedded with a therapeutic and an antioxidant. In some aspects, the polymer microparticle is formed of a polymer, a therapeutic, and an antioxidant. In some aspects, the antioxidant is BHT. In some aspects, the BHT is of about 0.01% to about 10% w/w of the polymer microparticle. In some aspects, the therapeutic is a limus drug. In certain aspects, the therapeutic is sirolimus. In further aspects, the therapeutic is sirolimus loaded at 35-45% w/w of the polymer microparticle. In some aspects, the PLGA is PLGA-DCM. In other aspect, the PLGA is PLGA-EtOAc. In some aspects, the polymer microparticle is of 10, 20, 30, 40, or 50

μm in average size and is of PLGA loaded with sirolimus at 35-45% w/w of the polymer microparticle. In other aspects, the polymer microparticle features at least one other polymer in addition to PLGA, selected from PLA, PLLA, PGA, PDLLA, PCL, PTMC, PEA, PPDO, and combinations thereof.

In certain aspects, the polymer microparticle of the present disclosure is of about 1 part drug, 1.5 parts polymer and 0.03 parts antioxidant. In some aspects, the polymer is PLGA. In certain aspects, the polymer is PLGA-EtOAc. In other aspects, the polymer is PLGA-DCM. In some aspects, the antioxidant is BHT. In some aspects, the drug is a limus drug. In certain aspects, the drug is sirolimus.

In some aspects of the present disclosure, the formulation can be of two or more different groups of polymer microparticles each of a polymer loaded or embedded with a therapeutic agent or drug. In some aspects, the two or more groups of polymer microparticles may differ in average size. In some aspects, the two or more groups are each of a uniform size or of a narrow distribution from a selected average size. In some aspects, the two or more groups of polymer microparticles may vary in the loaded or embedded therapeutic. In some aspects, the two or more groups of polymer microparticles may vary in surface morphology/drug loading, such as one group being prepared with DCM and the other with EtOAc. In some aspects, the two or more groups may vary in the bioabsorbable polymer used. In some aspects, the two or more groups of polymer microparticle may vary in PLGA composition, such as, for example and not by way of limitation, one being of PLGA 75:25 and the other being PLGA 50:50. In some aspects, the two or more polymer microparticles can vary in the amount or percentage of therapeutic loaded or embedded therein. In further aspects, the two or more groups can vary by two or more of surface morphology, drug loading amount, particle size, polymer composition, and therapeutic agent selection. In some aspects, the two or more groups can include the crystalline microparticles and the polymer microparticles as described herein.

In some aspects, the present disclosure concerns two or more groups of polymer microparticles of PLGA loaded or embedded with a limus drug that differ in average particle size, including PLGA-DCM and/or PLGA-EtOAc. In some aspects, one group of polymer microparticles is of an average particle size of 10 μm or about 10 μm or 10 μm±2 μm or 10 μm±1.5 μm or 10 μm±1.0 μm or 10 μm±0.5 μm or 10 μm±0.2 μm. In some aspects, one group of polymer microparticles is of an average particle size of 30 μm or about 30 μm or 30 μm±6 μm or 30 μm±5 μm or 30 μm±1.5 μm or 30 μm±1.0 μm or 30 μm±0.5 μm or 30 μm±0.2 μm. In some aspects the limus drug is sirolimus. In some aspects, the limus drug is loaded or embedded within the polymer microparticle at about 60%, at about 55% at about 50%, at about 45%, at about 40%, at about 35%, at about 30%, at about 25%, at about 20%, at about 15%, at about 10%, or at about 5% w/w of the polymer microparticle.

In some aspects, of the present disclosure, the formulation can be of two or more different groups of polymer microparticles each of a polymer loaded or embedded with a therapeutic, wherein the two or more groups are present in the formulation at a controlled ratio with respect to the other group(s). In some aspects, a first group is at a ratio of about 1:1 with the other group(s). In some aspects, the first group is in the formulation at a ratio of about 10:1, 9:1, 8:1, 7:1, 6:1, 5:1, 4:1, 3:1, 2:1, or 1:1 with the other group(s). In other aspects, the first group is in the formulation at a ratio of about 1:10, 1:9, 1:8, 1:7, 1:6, 1:5, 1:4, 1:3, 1:2, or 1:1 with the other group(s).

In some aspects, the present disclosure concerns formulations for coating the exterior surface of a balloon, wherein the formulation includes the polymer microparticles as described herein and an excipient. In some aspects, the formulation includes two or more groups of polymer microparticles as described herein and an excipient. In some aspects, the polymer microparticles are of about 40 to about 80% w/w of the formulation and the excipient is of about 5 to about 50% w/w of the formulation. In some aspects, the excipient is of about 5, 10, 15, 20, 25, 30, 35, 40, 45, or 50% w/w of the formulation. In some aspects, the excipient is of 5-45, 5-40, 5-35, 5-30, 5-25, 5, 20, 10-50, 10-40, 10-30, 20-50, 20-40, or 30-50% w/w of the formulation. In some aspects, the polymer microparticles are of 40, 45, 50, 55, 60, 65, 70, 75, 80% w/w of the formulation. In some aspects, the polymer microparticles are of 40-80, 40-75, 40-70, 40-60, 50-80, 50-75, 50-70, 50-65, 50-60, 60-80, 60-75, or 60-70% w/w of the formulation.

An excipient provides the coating formulation with good adhesion to the exterior surface of the balloon and further prevents the coating from detaching from the exterior surface of the balloon surface in pleating, folding, and handling. When drug coating is delivered to the target treatment site, excipient helps drug coating releasing from balloon surface and facilitates drug transfer from balloon surface to treated vessel.

In some aspects, the excipient is included as the coating formulation that is applied to the exterior surface of the balloon. In other aspects, the excipient becomes part of the formulation after application to the exterior surface of the balloon. In some aspects, one or more coating layer(s) on the balloon catheter may include an excipient or excipients. In some aspects, an excipient is applied simultaneously with the coating. In some aspects, an excipient may be applied prior to the microparticles. In other aspects, an excipient may be applied and/or coated on the microparticles. In one aspect, the formulation may include multiple excipients, for example, two, three, or four excipients. Examples of excipients may include semi-synthetic glycerides (e.g. Suppocire AIML, AML, BML, BS2, BS2X, NBL, NAIS 10, CS2X), lecithin, hydrogenated oils (e.g., vegetable, cottonseed, soybean), cetyl alcohol, tridecanol, witepol, cetyl palmiate, ethylene glycol distearate, glycerol monostearate, beeswax, paraffin, petroleum jelly, sodium docusate, hydrogenated coconut oil, coconut oil, mineral oil, petrolatum, decanol, soft paraffin, dodecanol, long chain saturated fatty acids, long chain unsaturated fatty acids, fatty acid esters, fatty acid ethers, solid lipids, methyl stearate, triglycerides, glyceryl monostearate, glyceryl palmitostearate, stearic acid, palmitic acid, decanoic acid, behenic acid, carnauba wax, paraffin, fatty acid triglycerides, fatty acid alcohols or combinations thereof. In some aspects, the excipient is one or more of petrolatum (petroleum jelly) and sodium docusate. In some aspects, the formulation is of two groups of polymer microparticles with a limus drug loaded therein and petrolatum. In some aspects, the formulation is of two groups of polymer microparticles with a limus drug loaded therein and sodium docusate. In some aspects, the formulation is of two groups of polymer microparticles with a limus drug loaded therein, sodium docusate, and petrolatum. In certain aspects, the limus drug is sirolimus. In certain aspects, a first group of polymer microparticles has an average size of about 10 μm. In certain aspects, a further group of polymer microparticles has an average size of about 30 μm or 35 μm. In further aspects, the first group of polymer microparticles and/or the second group of polymer microparticles is PLGA-EtOAc. In further aspects, the first group of polymer microparticles and/or the second group of polymer microparticles is PLGA-DCM. In some aspects, the polymer microparticles further include an antioxidant. In certain aspects, the antioxidant is BHT. The presence of an antioxidant in the polymer microparticle can be of benefit in protecting the polymer microparticles from degradation and/or oxidation.

In some aspects, the present disclosure concerns formulations for coating the exterior surface of a balloon, wherein the formulation includes the polymer microparticles as described herein, an excipient as described herein, and an antioxidant or a further antioxidant. In some aspects, the formulation includes two or more groups of polymer microparticles as described herein, an excipient as described herein, and an antioxidant or a further antioxidant. In some aspects, the formulation is of an excipient of petrolatum and/or sodium docusate and two or more groups of polymer microparticle, where the first group is PLGA-EtOAc of about 10 μm in average size with about 40% sirolimus loaded therein and with about 0.01 to 0.1 5 w/w BHT, and where the second group is PLGA-EtOAc of about 30 μm or 35 μm or 40 μm in average size with about 40% sirolimus loaded therein and with about 0.01 to 0.1% w/w BHT.

In some aspects, the formulation may be a coating solution or coating suspension that includes the formulations as described herein and a solvent, wherein the solvent evaporates from the exterior surface of the balloon to leave the formulation coated to the exterior surface of the balloon. Coating solvents may include, as examples, any combination of one or more of the following: water; alkanes such as pentane, cyclopentane, hexane, cyclohexane, heptane, and octane; aromatic solvents such as benzene, toluene, and xylene; alcohols such as methanol, ethanol, 2,2,2-trifluroethanol, propanol, and isopropanol, iso-butanol, n-butanol, tert-butanol, diethylamide, ethylene glycol monoethyl ether, trascutol, and benzyl alcohol; ethers such as dioxane, dimethyl ether, ethyl ether, diethyl ether, di-n-propyl ether, diisopropyl ether, t-butyl methyl ether, petroleum ether, and tetrahydrofuran; esters/acetates such as methyl acetate, ethyl acetate, isobutyl acetate, i-propyl acetate, and n-butyl acetate; ketones such as acetone, acetonitrile, diethyl ketone, cyclohexanone, and methyl ethyl ketones, methyl isobutyl ketone; chlorinated hydrocarbons such as chloroform, dichloromethane, ethylene dichloride; carbon tetrachloride, and chlorobenzene; dioxane; tetrahydrofuran; dimethylformamide; acetonitrile; dimethylsulfoxide; 1,6-dioxane; N,N-dimethylacetamide (DMA); diethylene glycol; diglyme; 1,2-dimethoxy ethane; hexamethylphosphoramide; and mixtures such as water/ethanol, water/acetone, water/methanol, water/tetrahydrofuran. In some aspects, the solvents is cyclohexane and/or heptane. The amount of coating solvent used depends on the coating process and viscosity, as the amount of solvent may affect the uniformity of the drug coating even though the coating solvent will be evaporated. In some aspects, the formulation may be applied two or more times to the exterior surface of the balloon of the balloon catheter, wherein sufficient time for the solvent to evaporate is provided in between applications of the formulation.

In some aspects, the solvent for coating is cyclohexane. In some aspects, the formulation includes a solvent, an excipient and two or more groups of polymer microparticles of PLGA, a limus drug, and an antioxidant. In certain aspects, the solvent is cyclohexane. In some aspects, the excipient is sodium docusate. In some aspects, the PLGA is PLGA-EtOAc and/or PLGA-DCM.

In some aspects, the formulation is of a coating solution of the formulation for the exterior surface of the balloon and a solvent. In some aspects, the coating solution is of a proportion wherein for every 5 mL of solvent, 150-162 mg of 10 μm PLGA-EtOAc with 40% w/w sirolimus and 0.01 to 0.1% w/w BHT polymer microparticles and 154-158 mg of 30/35/40 μm PLGA-EtOAc with 40% w/w sirolimus and 0.01 to 3% w/w BHT polymer microparticles, and 120-130 mg sodium docusate or petrolatum.

Balloon Catheters

In some aspects, the present disclosure concerns a balloon catheter with the formulations as disclosed herein on an exterior surface of the balloon of the balloon catheter. Referring to the example as depicted of FIG. 9, a balloon catheter 10 has a proximal end 18 and a distal end 20. The balloon catheter 10 may be any suitable catheter for desired use, including conventional balloon catheters known to one of ordinary skill in the art. For example, the balloon catheter 10 may be a rapid exchange or over-the-wire catheter. In some specific examples, the balloon catheter may be a BD ClearStream™ Peripheral catheter available from BD Peripheral Intervention. The balloon catheter 10 may be made of any suitable biocompatible material. The balloon 12 of the balloon catheter may include a polymer material, such as, for example only, polyvinyl chloride (PVC), polyethylene terephthalate (PET), polyethylene, Nylon, PEBAX (i.e. a copolymer of polyether and polyamide), polyurethane, polystyrene (PS), polyethyleneterephthalate (PETP), or various other suitable materials as will be apparent to those of ordinary skill in the art.

Figure 9:
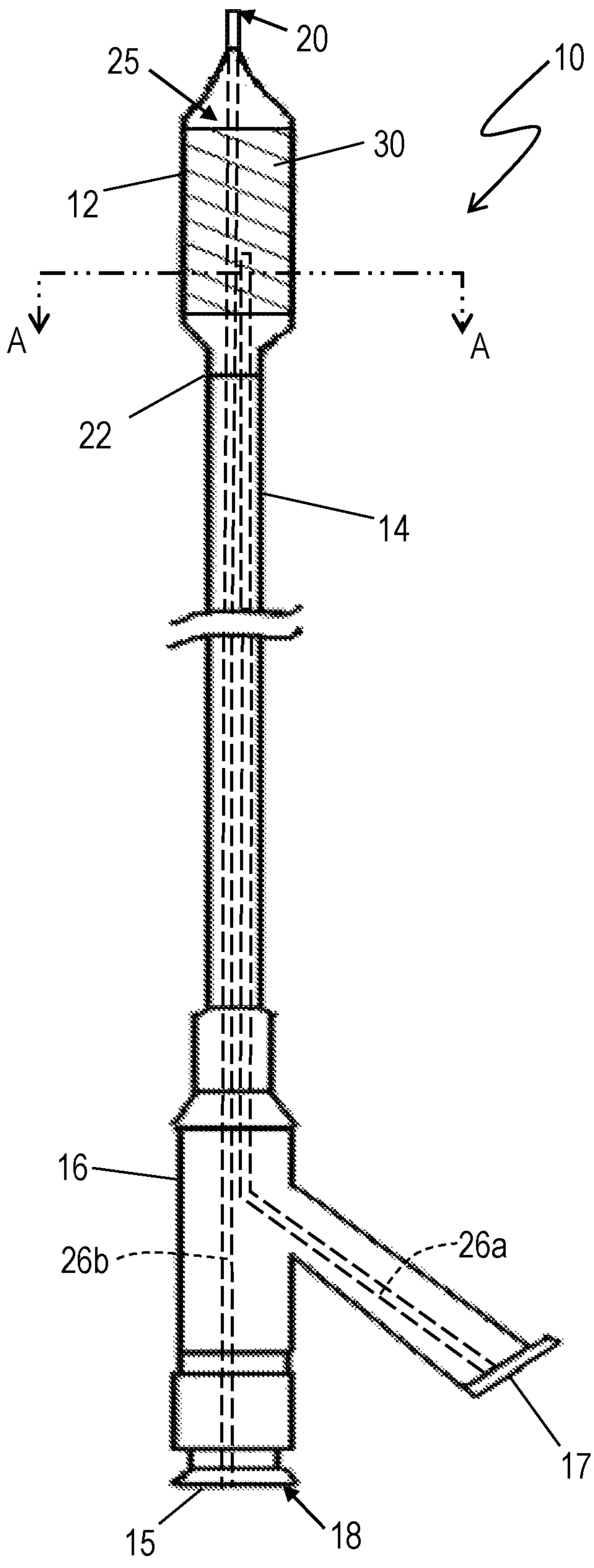
FIG. 9 is a schematic of an exemplary aspect of a medical device, particularly a balloon catheter, according to the present disclosure.
Figure 10A:
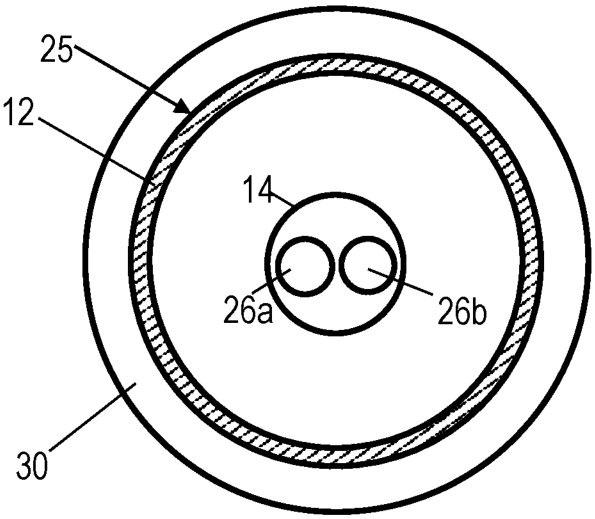
FIG. 10A is a cross-section of some aspect of the distal portion of the balloon catheter of FIG. 9, taken along line A-A, including a drug coating layer on an exterior surface of a balloon.
Figure 10B:
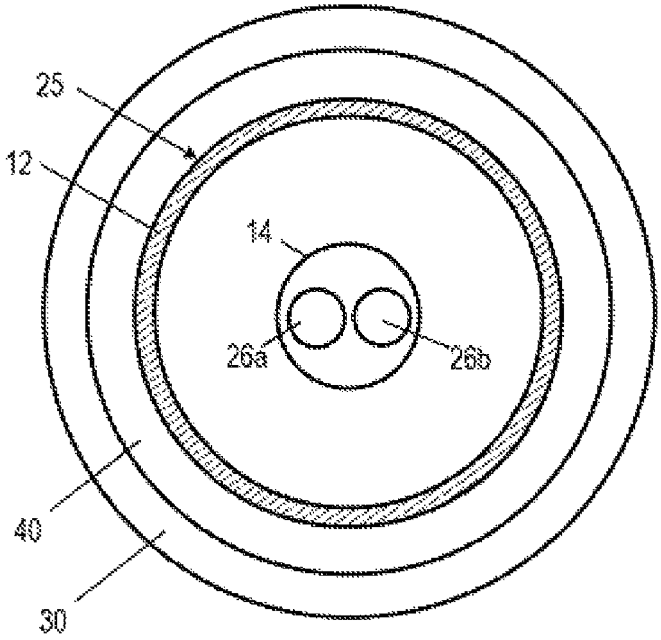
FIG. 10B and is a cross-section of some aspect of the distal portion of the balloon catheter of FIG. 9, taken along line A-A, including an intermediate layer between a exterior surface of the balloon and a drug coating layer.

Various facets of the balloon catheter 10 of FIG. 1 are illustrated through the cross sections along line A-A of FIG. 7 in FIGS. 10A and 10B. Referring jointly to FIGS. 9, 10A, and 10B, the balloon catheter 10 includes an expandable balloon 12 and an elongate member 14. The elongate member 14 extends between the proximal end 18 and the distal end 20 of the balloon catheter 10. The elongate member 14 has at least one lumen 26*a*, 26*b* and a distal end 20. The elongate member 14 may be a flexible member which is a tube made of suitable biocompatible material. The elongate member 14 may have one lumen or, as shown in FIGS. 9, 10A, and 10B, more than one lumen 26*a*, 26*b* therein. For example, the elongate member 14 may include a guide-wire lumen 26*b* that extends to the distal end 20 of the balloon catheter 10 from a guide-wire port 15 at the proximal end 18 of the balloon catheter 10. The elongate member 14 may also include an inflation lumen 26*a* that extends from an inflation port 17 of the balloon catheter 10 to the inside of the expandable balloon 12 to enable inflation of the expandable balloon 12. From the aspects of FIGS. 9, 10A, and 10B, even though the inflation lumen 26*a* and the guide-wire lumen 26*b* are shown as side-by-side lumens, it should be understood that the one or more lumens present in the elongate member 14 may be configured in any manner suited to the intended purposes of the lumens including, for example, introducing inflation media and/or introducing a guide-wire. Many such configurations are well known in the art.

The expandable balloon 12 is attached to the distal attachment end 22 of the elongate member 14. The expandable balloon 12 has an exterior surface 25 and is inflatable. The expandable balloon 12 is in fluidic communication with a lumen of the elongate member 14, (for example, with the inflation lumen 26*a*). At least one lumen of the elongate member 14 is configured to receive inflation media and to pass such media to the expandable balloon 12 for its expansion. Examples of inflation media include air, saline, and contrast media.

Still referring to FIG. 9, in one aspect, the balloon catheter 10 includes a handle assembly such as a hub 16. The hub 16 may be attached to the balloon catheter 10 at the proximal end 18 of the balloon catheter 10. The hub 16 may connect to and/or receive one or more suitable medical devices, such as a source of inflation media (e.g., air, saline, or contrast media) or a guide wire. For example, a source of inflation media (not shown) may connect to the inflation port 17 of the hub 16 (for example, through the inflation lumen 26*a*), and a guide wire (not shown) may be introduced to the guide-wire port 15 of the hub 16, (for example through the guide-wire lumen 26*b*).

In some aspects, the cross section A-A of FIG. 9 may be as depicted according to FIG. 10A, in which the formulation 30 is applied directly onto an exterior surface 25 of the balloon 12. The specific compositions of the formulation 30 itself, according to various aspects, will also be described subsequently in greater detail. In other example aspects, the cross section A-A of FIG. 1 may be as depicted according to FIG. 10B, in which the formulation 30 is applied onto an intermediate layer 40 overlying the exterior surface 25 of the balloon 12. In some aspects, the exterior surface 25 may undergo a surface modification. In aspects where the exterior surface 25 is a modified exterior surface, the exterior surface 25 has been subjected to a surface modification, such as a fluorine plasma treatment, which decreases a surface free energy of the exterior surface 25 before application of the formulation 30. Subjecting the exterior surface to a surface modification may decreases the surface free energy of the exterior surface before application of the coating layer and affect the release kinetics of drug in the formulation from the balloon, the crystallinity of the formulation, the surface morphology of the coated formulation and microparticle shape, or the microparticle size, drug distribution on the surface.

In aspects in which the cross section A-A of FIG. 9 is as depicted according to FIG. 10A, the balloon catheter 10 includes a formulation 30 applied over an exterior surface 25 of the balloon 12. The formulation 30 itself is described in various aspects herein.

In other aspects, two or more therapeutic agents are used in combination in the drug coating layer. In other aspects, the device may include a top layer (not shown) overlying the drug coating layer 30. In some aspects, a top coat layer may be advantageous in order to prevent premature drug loss during the device delivery process before deployment at the target site.

In some aspects, at least a portion of the exterior surface of the balloon of a balloon catheter is coated with a formulation as set forth herein. In some aspects, the formulation includes crystalline microparticles as described herein and a hydrophobic carrier and/or an excipient. In some aspects, the hydrophobic carrier is of petrolatum, semi-synthetic glycerides, lecithin, or combinations thereof and the excipient is sodium docusate. In some aspects, the crystalline microparticles are of about 20 to about 90% w/w of the formulation, the hydrophobic carrier is of about 15 to about 90% w/w of the formulation, and the excipient is of about 1 to about 60% w/w of the formulation. In some aspects, the formulation include polymer microparticles and an excipient. In some aspects, the polymer microparticles are of PLGA, such as PLGA-DCM and/or PLGA-EtOAc, sirolimus. In some aspects, the polymer microparticles are of PLGA, such as PLGA-DCM and/or PLGA-EtOAc, sirolimus, and BHT. In some aspects, the polymer microparticles are of about 40 to about 80% w/w of the formulation and the excipient is of about 5 to about 50% w/w of the formulation. In some aspects, the excipient is of about 5, 10, 15, 20, 25, 30, 35, 40, 45, or 50% w/w of the formulation. In some aspects, the excipient is of 5-45, 5-40, 5-35, 5-30, 5-25, 5, 20, 10-50, 10-40, 10-30, 20-50, 20-40, or 30-50% w/w of the formulation. In some aspects, the polymer microparticles are of 40, 45, 50, 55, 60, 65, 70, 75, 80% w/w of the formulation. In some aspects, the polymer microparticles are of 40-80, 40-75, 40-70, 40-60, 50-80, 50-75, 50-70, 50-65, 50-60, 60-80, 60-75, or 60-70% w/w of the formulation. In some aspects, sirolimus is of about 1 to about 65% w/w of the formulation, including about 2, 3, 4, 5, 6, 7, 8, 9, 10, 15, 20, 25, 30, 35, 40, 45, 50, 55, and 60% w/w of the formulation. In some aspects, PLGA is of about 30 to about 90% w/w of the formulation, including about 35, 40, 45, 50, 55, 60, 65, 70, 75, 80, and 85% w/w of the formulation. In some aspects, BHT is of about 0.001 to about 1% w/w of the formulation, including about 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, and 0.9% w/w of the formulation. In some aspects, sodium docusate is of about 5 to about 45% w/w of the formulation, including about 10, 20, 25, 30, 35, and 40% w/w of the formulation. In certain aspects, the formulation is of about 46-47% w/w of the formulation, sirolimus is of about 28-29% w/w of the formulation and sodium docusate is of about 28-30% w/w of the formulation.

In some aspects, the exterior surface of the balloon of the balloon catheter may include one or more additional elements. In some aspects, the additional elements may be applied as a coating layer. In some aspects, the coating layer may be applied to the exterior surface prior to the formulation(s) as described herein. In some aspects, the coating layer may be applied over or on top of an applied formulation. In some aspects, a coating layer may be applied between applications of the formulation.

In some aspects, one or more coating layer(s) may include a further excipient or excipients. In one aspect, the coating layer(s) may include multiple excipients, for example, two, three, or four excipients. Selection of the excipient or combination thereof may be based on the therapeutic agent, hydrophobic/hydrophilic layer materials, microparticle composition and/or coating solvent(s) used. As identified herein, the excipient or combination thereof can be included in the formulation(s) and mixed with coating solvent(s) to form a coating formulation, which is applied onto the exterior surface of the balloon of the balloon catheter. Alternatively or additionally, certain aspects may include applying the excipient(s) to the exterior surface of the balloon separately. In some aspects, the excipient or combination thereof may be applied to the balloon before the formulation(s). In some aspects, the excipient or combination thereof may be applied to after the therapeutic agent dissolved in the coating solvent. Without being bound by theory, the chosen excipient or combination thereof may be part of a coating mixture that adheres to the balloon exterior surface such that the coating does not fall off during handling and/or interventional procedure. Alternatively or additionally, the chosen excipient or combination thereof, when applied prior to or subsequently after the formulation(s), coating solvent, or coating solvents, should adhere to the formulation(s) and/or exterior surface of the balloon such that the coating does not fall off during handling and/or interventional procedure.

The relative amount of the excipient(s) in the coating layer(s) may vary depending on applicable circumstances. The optimal amount of the one or more excipients can depend upon, for example, the particular microparticles, therapeutic agent and other excipients selected, the critical micelle concentration of the surface modifier if it forms micelles, the hydrophilic-lipophilic-balance (HLB) of the excipients, the one or more excipients' octanol-water partition coefficient (P), the melting point of the excipients, the water solubility of the excipients and/or therapeutic agent and/or microparticles, the surface tension of water solutions of the surface modifier, etc. Other considerations will further inform the choice of specific proportions of the excipients. These considerations include the degree of bioacceptability of the excipients and the desired dosage of therapeutic agent to be provided.

In some aspects, the excipient may include a polymer. The polymer may be an anionic polymer. Examples of anionic polymers include polyglutamic acid or any block polymers containing the same, polyacrylic acid or any block polymers containing the same, polymethylacrylic acid or any block polymers containing same, polystyrene sulfonate or any block polymers containing the same, heparin, hyaluronic acid, and alginate. Without being bound by theory, if the formulation is cationic in nature, a coating including an anionic polymer may allow for the formulation to be retained for sustained drug release. Similarly, a cationic polymer for an anionic formulation may allow for the formulation to be retained for sustained drug release.

In further aspects, the excipient may be a biodurable polymer. As set forth herein, a biodurable polymer may include a polymer that is well tolerated and/or non-reactive when contacted to a subject or immune-reactive cells thereof and is resistant to erosion and/or enzymatic degradation and/or dissolution within the subject or the circulatory system thereof. Biodurable polymers include polyethylene terephthalate (PET), nylon 6,6, polyurethane (PU), polytetrafluoroethylene (PTFE), polyethylene (PE, low density and high density and ultra-high molecular weight, UHMW), polysiloxanes (silicones) and poly(methylmethacrylate) (PMMA) and Poly(vinylidene fluoride-co-hexafluoropropylene) (PVDF-HFP). In some aspects, the excipient may be PVDF-HFP. Without being bound by theory, utilizing a biodegradable polymers allows for the reduction or elimination of incomplete release of the formulation(s). In further aspects, the excipient may be a biodegradable polymer. As set forth herein, a biodegradable polymer may include a polymer that is well tolerated and/or non-reactive when contacted to a subject or immune-reactive cells thereof and is prone to erosion and/or enzymatic degradation and/or dissolution within the subject or the circulatory system thereof over a course of time. Examples of biodegradable polymers include polylactic acid polymers (PLA, PLLA, PDLA, PDLLA), polycaprolactone (PCL), poly lactic-co-glycolic Acid (PLGA), and poly(ethylene glycol) methyl ether-block-poly(lactide-co-glycolide) (PLGA-b-mPEG).

Suitable excipients that can be used in some aspects of the present disclosure include, without limitation, organic and inorganic pharmaceutical excipients, natural products and derivatives thereof (such as sugars, vitamins, amino acids, peptides, proteins, and fatty acids), surfactants (anionic, cationic, non-ionic, and ionic), and mixtures thereof. The following list of excipients useful in the present disclosure is provided for exemplary purposes only and is not intended to be comprehensive. Many other excipients may be useful for purposes of the present disclosure, such as polyglutamic acid, polyacrylic acid, hyaluronic acid, alginate, PVA, PVP, Pluronic (PEO-PPO-PEO), cellulose, CMC, HPC, starch, chitosan, human serum albumin (HSA), phospholipids, fatty acid, fatty acid esters, triglycerides, beeswax, cyclodextrin, polysorbates, polyethylene glycol, polyvinylpyrrolidone (PVP) and aliphatic polyesters.

In some aspects, the excipients may feature a drug affinity part. The drug affinity part provides an affinity to the therapeutic agent or microparticle by hydrogen bonding and/or van der Waals interactions. The excipients of the present disclosure may feature a hydrophilic part. As is well known in the art, the terms "hydrophilic" and "hydrophobic" are relative terms. To function as an excipient in some aspects of the present disclosure, the excipient is a compound that includes polar or charged hydrophilic moieties as well as non-polar hydrophobic (lipophilic) moieties. The hydrophilic part can accelerate diffusion and increase permeation of the therapeutic agent into tissue. The hydrophilic part of the excipient may facilitate rapid movement of formulation off the expandable medical device during deployment at the target site by preventing hydrophobic drug molecules from clumping to each other and to the device, increasing drug solubility in interstitial spaces, and/or accelerating drug passage through polar head groups to the lipid bilayer of cell membranes of target tissues.

An empirical parameter commonly used to characterize the relative hydrophilicity and hydrophobicity of an excipient is the hydrophilic-lipophilic balance ("HLB" value). Excipients with lower HLB values are more hydrophobic, and have greater solubility in oils, while surfactants with higher HLB values are more hydrophilic, and have greater solubility in aqueous solutions. Using HLB values as a rough guide, hydrophilic excipients are generally considered to be those compounds having an HLB value greater than about 10, as well as anionic, cationic, or zwitterionic compounds for which the HLB scale is not generally applicable. Similarly, hydrophobic excipients are compounds having an HLB value less than about 10. The HLB values of excipients in certain aspects are in the range of from about 0.0 to about 40, including about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39. It should be understood that the HLB value of an excipient is merely a rough guide generally used to enable formulation of industrial, pharmaceutical and cosmetic emulsions, for example. Keeping these inherent difficulties in mind, and using HLB values as a guide, excipients may be identified that have suitable hydrophilicity or hydrophobicity for use in aspects of the present disclosure, as described herein.

An empirical parameter commonly used in medicinal chemistry to characterize the relative hydrophilicity and hydrophobicity of pharmaceutical compounds is the partition coefficient, P, the ratio of concentrations of unionized compound in the two phases of a mixture of two immiscible solvents, usually octanol and water, such that P=([solute] octanol/[solute]water). Compounds with higher log Ps are more hydrophobic, while compounds with lower log Ps are more hydrophilic. Lipinski's rule suggests that pharmaceutical compounds having log P<5 are typically more membrane permeable. In certain aspects of the present disclosure, the excipient can possess a log P less than the log P of the therapeutic agent to be formulated. A greater log P difference between the therapeutic agent and the excipient can facilitate phase separation of the therapeutic agent. For example, if log P of the excipient is much lower than log P of the drug, the excipient may accelerate the release of therapeutic agent in an aqueous environment from the surface of a device to which the therapeutic agent might otherwise tightly adhere, thereby accelerating drug delivery to tissue during brief deployment at the site of intervention. In certain aspects of the present disclosure, log P of the excipient is negative. In other aspects, log P of the excipient is less than log P of the therapeutic agent. While a compound's octanol-water partition coefficient P or log P is useful as a measurement of relative hydrophilicity and hydrophobicity, it is merely a rough guide that may be useful in defining suitable excipients for use in some aspects of the present disclosure.

Exemplary excipients for application in the present disclosure may include chemical compounds with one or more hydroxyl, amino, carbonyl, carboxyl, acid, amide or ester moieties. Hydrophilic chemical compounds with one or more hydroxyl, amino, carbonyl, carboxyl, acid, amide or ester moieties having a molecular weight less than 5,000 to 10,000 are preferred in certain aspects. In other aspects, molecular weight of the excipient with one or more hydroxyl, amino, carbonyl, carboxyl, acid, amide, or ester moieties is preferably less than 1000 to 5,000, or more preferably less than 750 to 1,000, or most preferably less than 750. In these aspects, the molecular weight of the excipient is less than that of the therapeutic agent to be delivered.

In some aspects, the one or more excipients may be selected from amino alcohols, alcohols, amines, acids, amides and hydroxyl acids in both cyclo- and linear-aliphatic and aromatic groups. Examples include L-ascorbic acid and its salt, D-glucoascorbic acid and its salt, tromethamine, triethanolamine, diethanolamine, meglumine, glucamine, urea, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sugar alcohols, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), di(propylene glycol), tri(propylene glycol), tetra(propylene glycol, and penta(propylene glycol), and combinations thereof. Some of the chemical compounds with one or more hydroxyl, amine, carbonyl, carboxyl, amide or ester moieties described herein are very stable under heating, survive an ethylene oxide sterilization process, and/or do not react with the therapeutic agent during sterilization.

In some aspects, the one or more excipients may be selected from amino acids and salts thereof. For example, the excipient may be one or more of alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and derivatives thereof are. Certain amino acids, in their zwitterionic form and/or in a salt form with a monovalent or multivalent ion, have polar groups, relatively high octanol-water partition coefficients, and are useful in some facets of the present disclosure. In the context of the present disclosure "low-solubility amino acid" refers to amino acid having a solubility in unbuffered water of less than about 4% (40 mg/ml). These include cystine, tyrosine, tryptophan, leucine, isoleucine, phenylalanine, asparagine, aspartic acid, glutamic acid, and methionine.

Amino acid dimers, sugar-conjugates, and other derivatives may also be considered for excipients. Through simple reactions well known in the art hydrophilic molecules may be joined to hydrophobic amino acids, or hydrophobic molecules to hydrophilic amino acids, to make additional excipients useful in aspects of the present disclosure. Catecholamines, such as dopamine, levodopa, carbidopa, and DOPA, are also useful as excipients.

In some aspects, the excipient may be of a material that is at a glass transition temperature at 37° C. or higher. As identified herein, providing a material on the medical device that transitions to a sticky or tacky state in situ within the vessel of the subject allows for adhering the coating to the vessel wall. Such materials may include hydrogenated coconut oil, coconut oil, mineral oil, cetyl alcohol, petrolatum, petroleum jelly, decanol, soft paraffin, tridecanol, dodecanol, long chain saturated fatty acids, long chain unsaturated fatty acids, fatty acid esters, fatty acid ethers, witepsol, solid lipids, methyl stearate, triglycerides, glyceryl monostearate, glyceryl palmitostearate, stearic acid, palmitic acid, decanoic acid, behenic acid, beeswax, carnauba wax, paraffin, fatty acid triglycerides, fatty acid alcohols or combinations thereof.

In some aspects, the excipients may be liquid additives. One or more liquid excipients may be can be used in the medical device coating to improve the integrity of the coating. Without being bound by theory, a liquid excipient can improve the compatibility of the therapeutic agent in the coating mixture. The liquid excipients used in aspects of the present disclosure is not a solvent. The solvents such as ethanol, methanol, dimethylsulfoxide, and acetone, will be evaporated after the coating is dried. In other words, the solvent will not stay in the coating after the coating is dried. In contrast, the liquid excipients in aspects of the present disclosure will stay in the coating after the coating is dried. The liquid excipient is liquid or semi-liquid at room temperature and one atmosphere pressure. The liquid excipient may form a gel at room temperature. In some aspects, the liquid excipient may be a non-ionic surfactant. Examples of liquid excipients include PEG-fatty acids and esters, PEG-oil transesterification products, polyglyceryl fatty acids and esters, Propylene glycol fatty acid esters, PEG sorbitan fatty acid esters, and PEG alkyl ethers as mentioned above. Some examples of a liquid excipient are Tween 80, Tween 81, Tween 20, Tween 40, Tween 60, Solutol HS 15, Cremophor RH40, and Cremophor EL&ELP.

In some aspects, the excipient may be a surfactant; a chemical compound with one or more hydroxyl, amine, carbonyl, carboxyl, amides or ester moieties; or both. Exemplary surfactants may be chosen from PEG fatty esters, PEG omega-3 fatty esters and alcohols, glycerol fatty esters, sorbitan fatty esters, PEG glyceryl fatty esters, PEG sorbitan fatty esters, sugar fatty esters, PEG sugar esters, Tween 20, Tween 40, Tween 60, p-isononylphenoxypolyglycidol, PEG laurate, PEG oleate, PEG stearate, PEG glyceryl laurate, PEG glyceryl oleate, PEG glyceryl stearate, polyglyceryl laurate, polyglyceryl oleate, polyglyceryl myristate, polyglyceryl palmitate, polyglyceryl-6 laurate, polyglyceryl-6 oleate, polyglyceryl-6 myristate, polyglyceryl-6 palmitate, polyglyceryl-10 laurate, polyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG lauryl ether, Tween 20, Tween 40, Tween 60, Tween 80, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside and their derivatives.

By incorporating the one or more additional excipients, the formulation may have increased stability during transit and rapid drug release when pressed against tissues of the lumen wall at the target site of therapeutic intervention when compared to some formulations comprising the therapeutic agent and only one excipient. Furthermore, the miscibility and compatibility of the formulation with the excipient, generally, is improved by the presence of one or more additional excipients. For example, a surfactant may allow for improved coating uniformity and integrity.

In some aspects, the coating(s) may include multiple excipients, and one excipient is more hydrophilic than one or more of the other excipients. In another aspect, the coating comprises multiple excipients, and one excipient has a different structure from that of one or more of the other excipients. In another aspect, the coating comprises multiple excipients, and one excipient has a different HLB value from that of one or more of the other excipients. In yet another aspect, the coating comprises multiple excipients, and one excipient has a different Log P value from that of one or more of the other excipients.

Some aspects of the present disclosure may include a mixture of at least two additional excipients, for example, a combination of one or more surfactants and one or more chemical compound with one or more hydroxyl, amine, carbonyl, carboxyl, amides or ester moieties. For example, some surfactants may adhere so strongly that the formulation is not able to rapidly release from the surface of the medical device at the target site. On the other hand, some may adhere so poorly to the balloon's exterior surface that they release the formulation before it reaches the target site, for example, into serum during the transit of a coated balloon catheter to the site targeted for intervention. By incorporating a mixture of multiple excipients, the coating may have improved properties over a formulation with only one excipient or no excipient. In some aspects, the at least two additional excipients may include one of sodium docusate, sorbitol, urea, BHT, BHA, PEG-sorbitan monolaureate, petrolatum, methyl stearate or a combination thereof.

In some aspects, the one or more additional excipients may include an antioxidant. An antioxidant is a molecule capable of slowing or preventing the oxidation of other molecules. Oxidation reactions can produce free radicals and/or peroxides, which start chain reactions and may cause degradation of therapeutic agents. Antioxidants terminate these chain reactions by removing free radicals and inhibiting oxidation of the active agent by being oxidized themselves. Antioxidants are used as the one or more additional excipients in certain aspects to prevent or slow the oxidation of the therapeutic agents in the coatings for medical devices. Antioxidants are a type of free radical scavengers. The antioxidant may be used alone or in combination with other additional excipients in certain aspects and may prevent degradation of the active therapeutic agent during sterilization or storage prior to use. Some representative examples of antioxidants that may be used in the drug coatings of the present disclosure include, without limitation, oligomeric or polymeric proanthocyanidins, polyphenols, polyphosphates, polyazomethine, high sulfate agar oligomers, chitooligosaccharides obtained by partial chitosan hydrolysis, polyfunctional oligomeric thioethers with sterically hindered phenols, hindered amines such as, without limitation, p-phenylene diamine, trimethyl dihydroquinolones, and alkylated diphenyl amines, substituted phenolic compounds with one or more bulky functional groups (hindered phenols) such as tertiary butyl, arylamines, phosphites, hydroxylamines, and benzofuranones. Also, aromatic amines such as p-phenylenediamine, diphenylamine, and N,N' disubstituted p-phenylene diamines may be utilized as free radical scavengers. Other examples include, without limitation, butylated hydroxytoluene ("BHT"), butylated hydroxyanisole ("BHA"), L-ascorbate (Vitamin C), Vitamin E, herbal rosemary, sage extracts, glutathione, resveratrol, ethoxyquin, rosmanol, isorosmanol, rosmaridiphenol, propyl gallate, gallic acid, caffeic acid, p-coumeric acid, p-hydroxy benzoic acid, astaxanthin, ferulic acid, dehydrozingerone, chlorogenic acid, ellagic acid, propyl paraben, sinapic acid, daidzin, glycitin, genistin, daidzein, glycitein, genistein, isoflavones, and tertbutylhydroquinone. Examples of some phosphites include di(stearyl)pentaerythritol diphosphite, tris(2,4-di-tert.butyl phenyl)phosphite, dilauryl thiodipropionate and bis(2,4-di-tert.butyl phenyl)pentaerythritol diphosphite. Some examples, without limitation, of hindered phenols include octadecyl-3,5,di-tert.butyl-4-hydroxy cinnamate, tetrakis-methylene-3-(3',5'-di-tert-.butyl-4-hydroxyphenyl)propionate methane 2,5-di-tert-butylhydroquinone, ionol, pyrogallol, retinol, and octadecyl-3-(3,5-di-tert.butyl-4-hydroxyphenyl)propionate. An antioxidant may include glutathione, lipoic acid, melatonin, tocopherols, tocotrienols, thiols, Beta-carotene, retinoic acid, cryptoxanthin, 2,6-di-tert-butylphenol, propyl gallate, catechin, catechin gallate, and quercetin. Preferable antioxidants are butylated hydroxytoluene (BHT) and butylated hydroxyanisole (BHA).

Methods

In some aspects, the present disclosure includes methods if preparing the microparticles, the formulations and the balloons as described herein.

In some aspects, the present disclosure concerns crystalline microparticles. Crystalline microparticles can be obtained by grinding down limus drug crystals to desired particle sizes. Grinding can be achieved through devices such as Jaw Crushers, Rotor Mills, Cutting and Knife Mills, Disc Mill, Mortar Grinder, and Ball mills. The process for achieving crystalline microparticles can be through dry milling, wet milling and/or cryo-milling. Following the grinding, microparticles of a particular desired size can be achieved through size selection processes, such as meshing, sieving, weight selection, and filtration.

In some aspects, the present disclosure concerns formulations that include a hydrophobic carrier with crystalline microparticles on the surface of a balloon. In some aspects, the formulation can be prepared by adding the hydrophobic carrier and the crystalline microparticles in an organic or hydrophobic solvent. In such a solvent, the crystalline microparticles does not dissolve, but the hydrophobic carrier does. The solution can then be applied to the exterior surface and as the solvent evaporates, the hydrophobic carrier emerges from the applied solution and retains the crystalline microparticles on the exterior surface of the balloon. In some aspects, the hydrophobic carrier is of petrolatum and the crystalline microparticles are of sirolimus.

In some aspects, the present disclosure concerns polymer microparticles with a therapeutic loaded or embedded therein. In some aspects, the polymer microparticles are formed through preparing a solution of a therapeutic and a polymer in a solvent and allowing the solvent to evaporate. In some aspects, an antioxidant, such as BHT may also be included in the formation of a polymer microparticle. Through techniques such as microfluidics and membrane emulsification, it is possible to control the size of polymer microparticle formed. For example, polymer microparticle size and size distribution can be controlled by the dispersing phase flow rate, the continuous phase flow rate, the microfluidic chip channel size, and the solid percentage in the dispersing phase. In evaporative emulsion, polymer microparticle size and size distribution can be controlled by the dispersing phase injection rate, the stirring rate in the continuous phase reservoir, the membrane pore size, and the solid percentage in the dispersing phase. The general method to make polymer microparticles includes: weighing and dissolving sirolimus, PLGA and BHT in a solvent (such as DCM or EtOAc) to form a disperse phase; weighing and dissolving polyvinyl alcohol in water to form a continuous phase; injecting the disperse phase via either microfluidics or membrane emulsification into the continuous phase to form disperse phase droplets in the continuous phase; evaporating the solvent; collecting the polymer microparticles either by filtration, lyophilization or centrifuge; and, drying the polymer microparticles.

In some aspects, the present disclosure concerns solvents and the selection thereof for applying the coating(s) as set forth herein to the balloon. Solvents for preparing of the coatings, which are referred to herein as "coating solvents," are used to dissolve the coating or a part thereof and apply to the balloon surface. The dissolved portions within the coating solvent together make up a "coating mixture," which is coated onto the balloon.

In some aspects, the coating solvent may be any solvent or combination of solvents that are suitable to dissolve the hydrophobic material(s) of the formulation coating. In further aspects, the coating solvent may be any solvent or combination of solvents that are suitable to dissolve the hydrophobic material(s) and the therapeutic agent(s). As identified herein, in some aspects, the therapeutic agent is provided to the surface of the medical device by preparing a mixture or slurry of the microparticles suspended in a solution of the hydrophobic material dissolved in solvent. The non-dissolved therapeutic may be of a crystalline form, an amorphous form, or loaded within a microparticle as described herein wherein the microparticle and/or the therapeutic loaded therein does not dissolve in the solvent. Evaporation of the solvent from the surface of the medical device therefore leaves the hydrophobic or hydrophilic layer with the therapeutic suspended therein.

In some aspects, coating solvents may include, as examples, any combination of one or more of the following: water; alkanes such as pentane, cyclopentane, hexane, cyclohexane, heptane, and octane; aromatic solvents such as benzene, toluene, and xylene; alcohols such as methanol, ethanol, 2,2,2-trifluroethanol, propanol, and isopropanol, iso-butanol, n-butanol, tert-butanol, diethylamide, ethylene glycol monoethyl ether, trascutol, and benzyl alcohol; ethers such as dioxane, dimethyl ether, ethyl ether, diethyl ether, di-n-propyl ether, diisopropyl ether, t-butyl methyl ether, petroleum ether, and tetrahydrofuran; esters/acetates such as methyl acetate, ethyl acetate, isobutyl acetate, i-propyl acetate, and n-butyl acetate; ketones such as acetone, acetonitrile, diethyl ketone, cyclohexanone, and methyl ethyl ketones, methyl isobutyl ketone; chlorinated hydrocarbons such as chloroform, dichloromethane, ethylene dichloride; carbon tetrachloride, and chlorobenzene; dioxane; tetrahydrofuran; dimethylformamide; acetonitrile; dimethylsulfoxide; 1,6-dioxane; N,N-Dimethylacetamide (DMA); diethylene glycol; diglyme; 1,2-dimethoxy ethane; hexamethylphosphoramide; and mixtures such as water/ethanol, water/acetone, water/methanol, water/tetrahydrofuran. The amount of coating solvent used depends on the coating process and viscosity, as the amount of solvent may affect the uniformity of the drug coating even though the coating solvent will be evaporated.

Various techniques may be used for applying a coating solution or coating mixture to a medical device such as metering, casting, spinning, spraying, dipping (immersing), rolling, ink jet printing, 3D printing, electrostatic techniques, plasma etching, vapor deposition, and combinations of these processes. Choosing an application technique principally depends on the viscosity and surface tension of the coating solution or coating mixture. In aspects of the present disclosure, metering, dipping and spraying may be preferred because it makes it easier to control the uniformity of the thickness of the drug coating as well as the concentration of the therapeutic agent applied to the medical device. Regardless of whether the coating solution or coating mixture is applied by spraying or by dipping or by another method or combination of methods, each layer may be applied to the medical device in multiple application steps in order to control the uniformity and the amount of therapeutic substance and additive applied to the medical device.

Each applied layer may have a thickness from 0.1 μm to 15 μm, from 0.1 μm to 10 μm, from 0.1 μm to 5 μm, from 0.1 μm to 1 μm, from 1 μm to 15 μm, from 1 μm to 10 μm, from 1 μm to 5 μm, from 5 μm to 15 μm, from 5 μm to 10 μm, or from 10 μm to 15 μm. The total number of layers applied to the medical device is in a range of from 1 to 50, from 1 to 40, from 1 to 30, from 1 to 20, from 1 to 10, from 10 to 50, from 10 to 40, from 10 to 30, from 10 to 20, from 20 to 50, from 20 to 40, from 20 to 30, from 30 to 40, or from 40 to 50. In some aspects, only one layer is applied to the medical device. In some aspects, more than one layer is applied to the medical device. The total thickness of the coating may be from 0.1 μm to 200 μm, from 0.1 μm to 150 μm, from 0.1 μm to 100 μm, from 0.1 μm to 50 μm, from 0.1 μm to 10 μm, from 0.1 μm to 1 μm, from 1 μm to 200 μm, from 1 μm to 150 μm, from 1 μm to 100 μm, from 1 μm to 50 μm, from 1 μm to 10 μm, from 10 μm to 200 μm, from 10 μm to 150 μm, from 10 μm to 100 μm, from 10 μm to 50 μm, from 50 μm to 200 μm, from 50 μm to 150 μm, from 50 μm to 100 μm, from 100 μm to 200 μm, from 100 μm to 150 μm, or from 150 μm to 200 μm. In other aspects, the secondary water-soluble coat is applied after the drug-coating solvent has evaporated. In further aspects, the secondary water-soluble coating is applied before the solvent of the drug-coating layer has evaporated.

In some aspects, the present disclosure concerns formulations of the polymer microparticles and an excipient, such as petrolatum and/or sodium docusate. In some aspects, the formulation is formed through mixing the polymer microparticles and excipient in a solvent, such as cyclohexane and/or heptane, and allowing evaporation of the solvent. In some aspects, the solvent evaporates after application on the surface of a balloon.

In some aspects, the methods of preparing a coated balloon include the following steps of: electing a solvent (or a mixture of solvents) which is able to dissolve the excipient (s), but not the drug; selecting polymer microparticles or groups thereof in a desired particle size and size distribution; mixing the polymer microparticles and the excipient with the selected solvent (or solvents) to form a drug coating suspension; cleaning the balloon surface with a solvent; applying the drug coating suspension on the balloon; and evaporating the solvent. In some aspects, the methods may also include steps for application in a human subject to sterilize and package the balloon prior to use. Such may include: pleating and folding the formulation-coated balloon, inserting the folded balloon into a balloon protection sheath; inserting the balloon catheter inside a hoop; packaging the balloon catheter into a dual pouch for sterilization; adding a desiccator pack and oxygen absorber in the pouch; and, sealing the pouch.

In some aspects, the present disclosure concerns formulations that allow for reduced degradation of the therapeutic agent during sterilization and/or storage of the prepared balloon catheters. Through the embedding within the polymer microparticles and/or hydrophobic carrier, along with the presence of an antioxidant and/or excipient, the balloon catheter may avoid some or all of the degradative effects to be expected from sterilization and/or storage of the balloon catheter prior to use within a subject.

In some aspects, the present disclosure concerns providing the balloon catheter to a subject. In some aspects, the balloon catheter is provided to the subject to treat or alleviate vascular stenosis. In some aspects, the balloon catheter is provided to treat and/or alleviate non-vascular stenosis and strictures, such as chronic sinusitis, asthma, chronic pulmonary obstruction, urethra stricture, bladder-neck stricture, and/or intestinal restructure.

Microparticle Coating Methods

In some aspects, the method for coating the balloon of the balloon catheter include application of a slurry or a mixture of solid microparticles in a solution, such as the crystalline and/or polymer microparticles as set forth herein. In some aspects, a slurry may require one or more additional steps to provide an even coating to the exterior surface of the balloon of a balloon catheter. For example, it may be appreciated that the crystalline microparticles and/or polymer microparticles can sediment in solution due to their mass and/or density. Uniform coating requires not only uniformity of the microparticles across the coated portion of the exterior surface of the balloon, but also uniformity between balloons, such that a user can expect the balloon of one balloon catheter to provide effects consistent with the balloon of a second balloon catheter.

In some aspects, the methods include agitation of a slurry of microparticles in a solution to prevent sedimentation thereof. Agitation can be achieved through stirring and/or shaking of a container holding or retaining the slurry. It will be appreciated that agitation is to be of sufficient intensity to avoid sedimentation of the microparticles. In some aspects, agitation is limited in intensity to minimize the collision force and/or erosion between microparticles so that the integrity of their size and composition is maintained. In certain aspects, the slurry solution is stirred prior to coating the balloon. In some aspects, the balloon is pre-treated or wetted with the solvent of the slurry solution prior to application of the slurry solution.

In some aspects, the methods of coating the microparticles on the balloon may include stirring of a slurry solution prior to application on the exterior of the balloon. In some aspects, the stirring may be achieved by magnetic stirring using a ferromagnetic stirrer or rod and a rotating magnetic field. In other aspects, stirring can be achieved with a motor operated stirrer or rod, such as at a rate of between about 300 and about 3000 rpm, or of about 500 to 1000 rpm. In some aspects, the slurry can be sonically agitated.

In some aspects, the methods for coating the microparticles may include dispensing the slurry from the lumen of a tip or nozzle connected to an operable dispenser that can control flow of the slurry to allow for uniform application. The tip may be operably connected to a reservoir of retained slurry in the dispenser, such as a barrel. The barrel may be part of a syringe or the body of a pipette or similar. Flow of the slurry from the tip may be controlled by manual pressurized displacement or mechanical pump displacement or application of a force to the barrel, such as with a plunger, to eject the slurry from the barrel in a controlled and/or even manner. In some aspects, the slurry is agitated within the barrel of the dispenser and application of a force allows for the slurry to flow from the barrel through the lumen of the tip and on to the balloon's exterior surface. In other aspects, the slurry is agitated by stirring in an external container, drawing the slurry into the barrel and then releasing or flowing the slurry from the barrel through the lumen of the tip and onto the exterior of the balloon. In some aspects, the slurry may be agitated prior to being introduced into the barrel and within the barrel itself. Examples of barrels with agitating means therein include products by Sono-Tek (Milton, NY) and Cetoni (Korbussen, Germany).

In some aspects, the methods may include agitation of the slurry prior to placement within the barrel of the dispenser. In some aspects, the slurry is drawn into the barrel of the dispenser by an applied force such as pumping or suction. In some aspects, the slurry is drawn into the barrel through the lumen of the tip or nozzle. In some aspects, the slurry is drawn from a container that retains the slurry. In some aspects, the container is cylindrical or partially cylindrical with a flat bottom to prevent sedimentation, such as with abscesses or corners where agitation is less or reduced. In some aspects, the stirrer may be of the diameter of the cylindrical bottom to reduce sedimentation. In other aspects, the container and/or stirrer can be moved during agitation to allow the stirrer to contact the cylindrical walls to reduce sedimentation.

In some aspects, the methods of coating the balloon include controlling for solvent evaporation between preparing the formulation and coating the balloon, the angle and duration of coating the slurry on the balloon, the number of uses for each tip, rinses and the number thereof between applications of coating slurry and/or between balloons, the material of the tip or nozzle, and positioning in the container for withdrawal of the slurry. In some aspects, the methods may include wetting the lumen of the tip or nozzle with the slurry and/or the solvent of the slurry.

In some aspects, the methods include pipetting the slurry on the exterior surface. In some aspects, the methods may include a maintained number of wetting or priming rinses, a maintained material of pipette, a maintained direction of slurry application and a maintained number of passes along the balloon. The methods may further include application of a new pipette for each balloon being coated. In some aspects, the pipette is a 2-stop pipette or similar that allows for sufficiently wetting or priming the barrel of the pipette beyond the volume to be dispensed. In some aspects, the pipette is a two-stop pipette, wherein the first stop expels a selected volume and the second expels all liquid. In some aspects, the method includes agitating the slurry and then drawing the slurry into the barrel of the pipette. In some aspects, the pipette can be primed, such as by depressing to the first stop, placing the tip in the slurry, depressing to the second stop and releasing the pipette plunger to draw the slurry in. the barrel. The pipette tip is then withdrawn from the slurry and the plunger depressed to the second stop to expel all slurry therein and optionally repeating the expulsion. The slurry can then be drawn back into the barrel by pressing to the first stop, replacing the tip in the slurry and releasing the plunger. The slurry can then be coated by holding the tip at about a 450 angle, a horizontal angle, or a vertical angle and moving from the proximal to distal ends of the balloon along the length of the underlying catheter in a controlled time with even application of the plunger. In some aspects, the slurry solution is dispensed at a rate of about 3-100 μL/s as the tip move along the length of the balloon at a rate of about 1-5 cm/s or of over a period about 5-30 seconds per length of balloon (based on a balloon length of about 80 to about 250 mm) along the length of the balloon Any residual fluid is expelled once the distal end is reached in a single pass along the length of the balloon, with to contact of the tip itself to the balloon to spread the applied slurry. The pipette tip is changed and a further balloon may be coated with a new tip following the same priming procedures. As demonstrated in the examples, using the same tip provides for inconsistent application. As also demonstrated in the examples, varying the number of pre-wetting rinses can also provide for inconsistent application.

In some aspects, the slurry is applied using a syringe with a stirring mechanism or sonicator therein. In some aspect, the syringe is part of an automated arrangement wherein the user loads a balloon and the slurry is applied through an automated process. In some aspects, the automation process may require attention to the rate of dispensing the slurry, the angle of dispensing, the speed of agitation, and the tubing size.

EXAMPLES

Example 1: Polymer Microparticle Morphology

Figure 2:
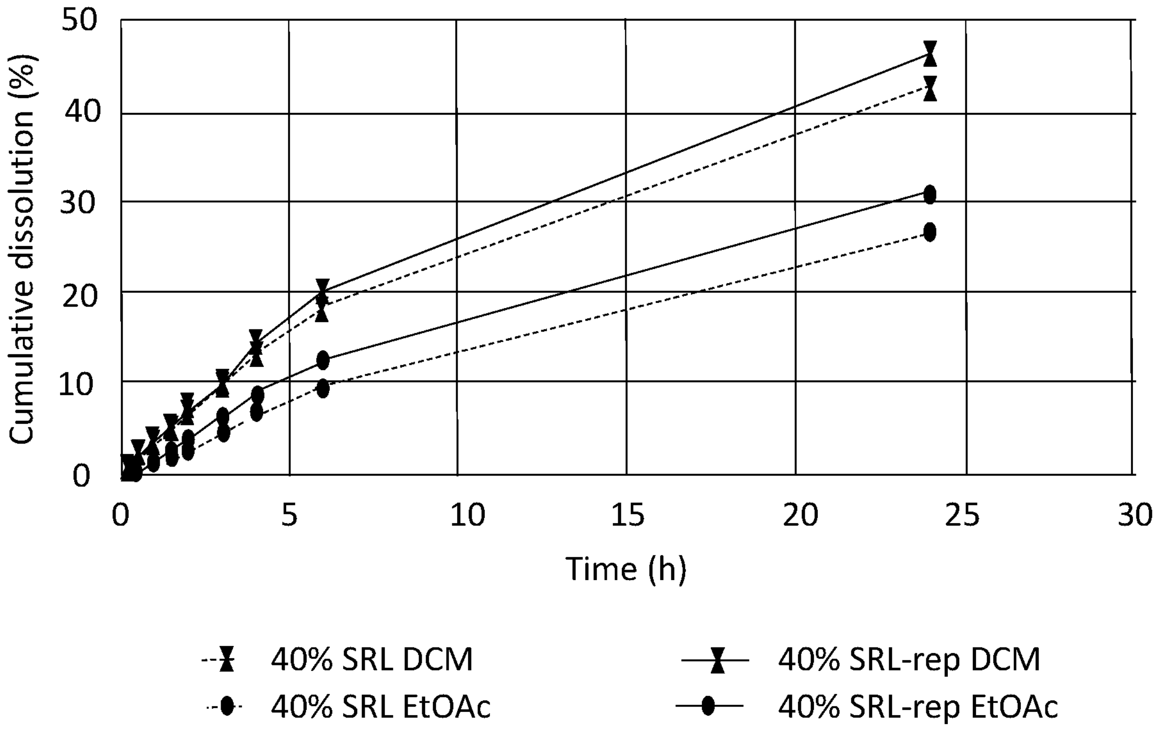
FIG. 2 depicts sirolimus dissolution from beads made with dichloromethane (DCM) and ethyl acetate (EtOAc).

Experiments were performed to observe potential difference is preparing microparticles with different solvents. Work was carried out with dichloromethane (DCM) and Ethyl acetate (EtOAc) as solvents. Raman spectroscopy was performed to characterize the drug distribution within the microspheres using these two solvents. FIGS. 1A and 1B show the SEM images and FIGS. 1C and 1D show Raman maps of the two solvents utilized in the bead manufacturing process. FIG. 2 shows the dissolution of sirolimus from the different polymer microparticles The microparticles presented in FIGS. 1A-D and FIG. 2 are of an average size of approximately 35 microns with a 40% drug loading and with a PLGA 75:25, (Evonik, Resomer RG 756 S) with a molecular weight range of 76,000 to 115,000 polymer.

Example 2: Particle Size and Drug Loading Amount Release Rates

PLGA (poly(lactate-co-glycolic acid)) loaded sirolimus microspheres were made by a single emulsion (Oil/Water) process by dissolving PLGA polymer in dichloromethane (DCM) at room temperature. Sirolimus drug was then added into the polymer solution and stirred until all sirolimus is completely dissolved. The PLGA/sirolimus solution was used for droplet phase. 1% (w/v) PVA (polyvinyl alcohol) was used for continuous (water) phase for the microsphere process. The two solutions were fed into a Dolomite (Royston, UK) microfluidic system to make different microsphere sizes. After the microspheres are collected in 1% w/v PVA solution, the microspheres were continuously stirred overnight at room temperature to evaporate off DCM. The microspheres were filtered and dried in desiccator under vacuum overnight.

The microspheres were then tested for drug elution in-vitro. FIG. 3 shows PLGA-DCM/sirolimus elution profiles of different sizes. The PLGA used here was PLGA 75:25 (Resomer RG 756 S with a molecular weight range of 76,000 to 115,000). This data also compares how sirolimus dissolution is effected by drug loading: 30 μm PLGA with 40% sirolimus versus 30 μm PLGA with 60% sirolimus.

Figure 4:
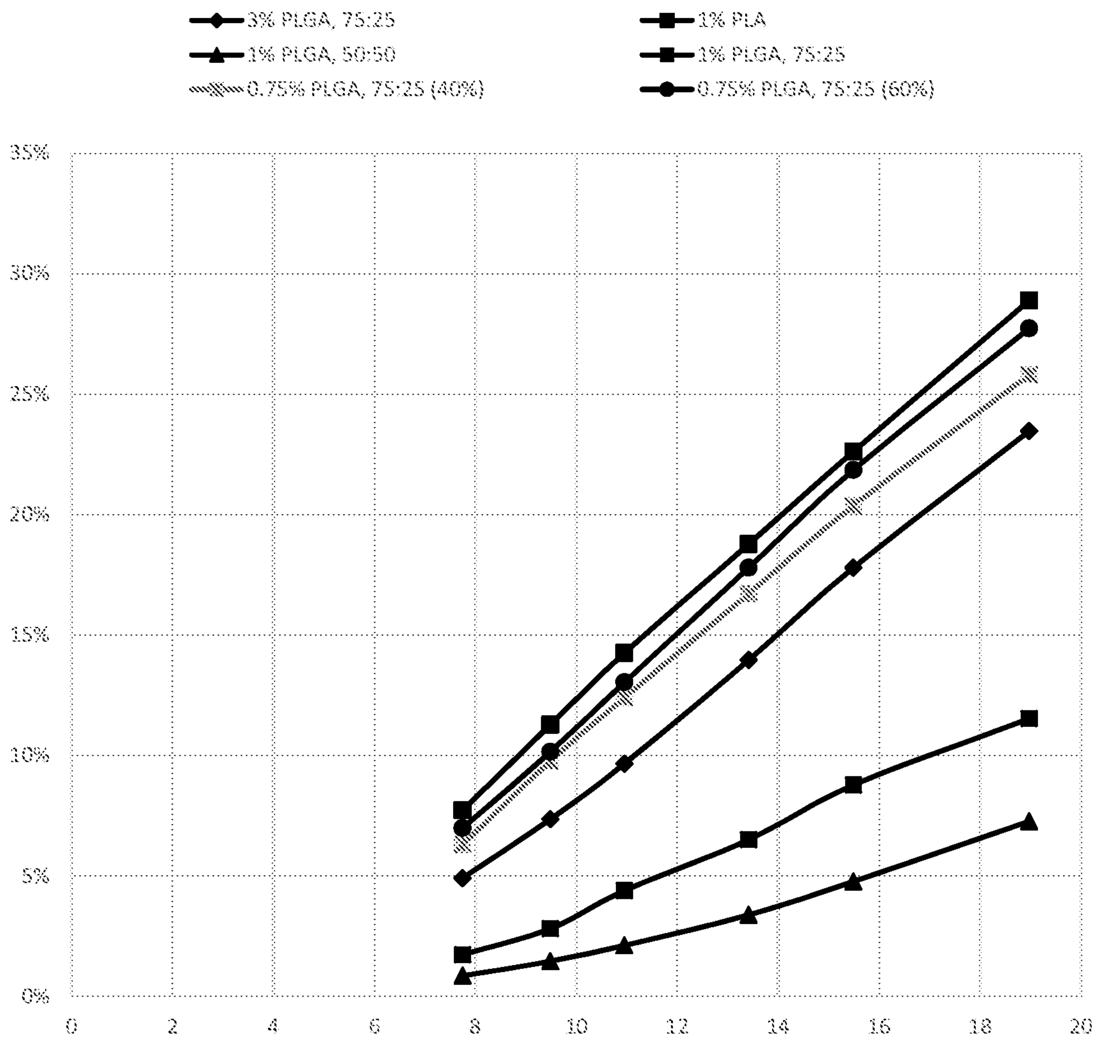
FIG. 4 depicts elution of sirolimus from the identified polymer compositions and varied drug loading.

Various types of polymer with varying degradation rates were also used to depict the dependency of sirolimus dissolution to polymer type. FIG. 4 shows comparisons with PLGA 75:25, (Evonik, Resomer RG 756 S) with a molecular weight range of 76,000 to 115,000, PLGA 50:50, (Sigma-Aldrich, P2191) with a molecular weight range of 30,000 to 60,000, and PLA (poly(L-lactide)) (Evonik, Resomer L 206 S). FIG. 4 highlights the dependency of sirolimus dissolution on the polymer used. The data in FIG. 4 also compares the effect of drug loading on dissolution for two identical particle makeups: 0.75% PLGA, 75:25 at 40% sirolimus loading and 0.75% PLGA, 75:25 at 60% sirolimus. Table 1 presents an overview of the microparticles assessed.

TABLE 1

| Microparticle | Average Bead Size (Standard deviation) microns | Drug loading by weight |
|---|---|---|
| 3% PLGA, 75:25 | 23.7 (9.52) | 40% |
| 1% PLGA 75:25 | 15.1 (6.9) | 40% |
| 1% PLGA 50:50 | 9.0 (8.9) | 40% |
| 1% PLA | 15.2 (6.2) | 40% |
| 0.75% PLGA, 75:25 (40%) | 20.1 (5.1) | 40% |
| 0.75% PLGA, 75:25 (60%) | 20.4 (7.2) | 60% |

Figure 5:
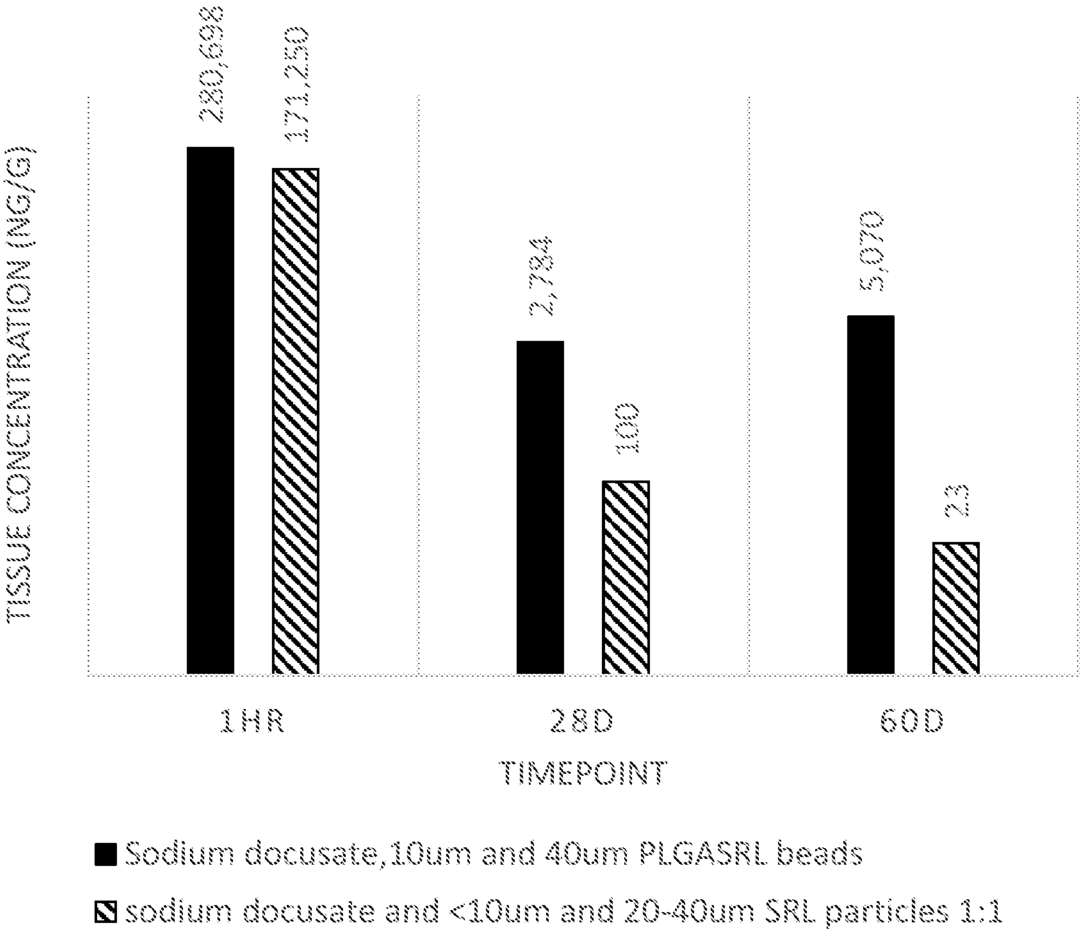
FIG. 5 depicts preclinical, arterial pharmacokinetic data from an animal study comparing PLGA sirolimus beads (solid bars) versus sirolimus crystals (diagonal stripe bars).

An animal study next compared PLGA 75:25, (Evonik, Resomer RG 756 S) with a molecular weight range of 76,000 to 115,000 polymer loaded microspheres of two size distributions (approximately 10 and approximately 40 microns) with ground crystalline sirolimus particles of two size distributions (<10 microns and 20-40 microns). The two formulations had the same drug load (3 $\mu g/mm^2$) and the same excipient, sodium docusate. The animal model was a healthy porcine model. This data set suggest that PLGA/sirolimus microspheres have a higher rate of transfer and retention at the target lesion as opposed to sirolimus crystals (FIG. 5).

Figure 6:
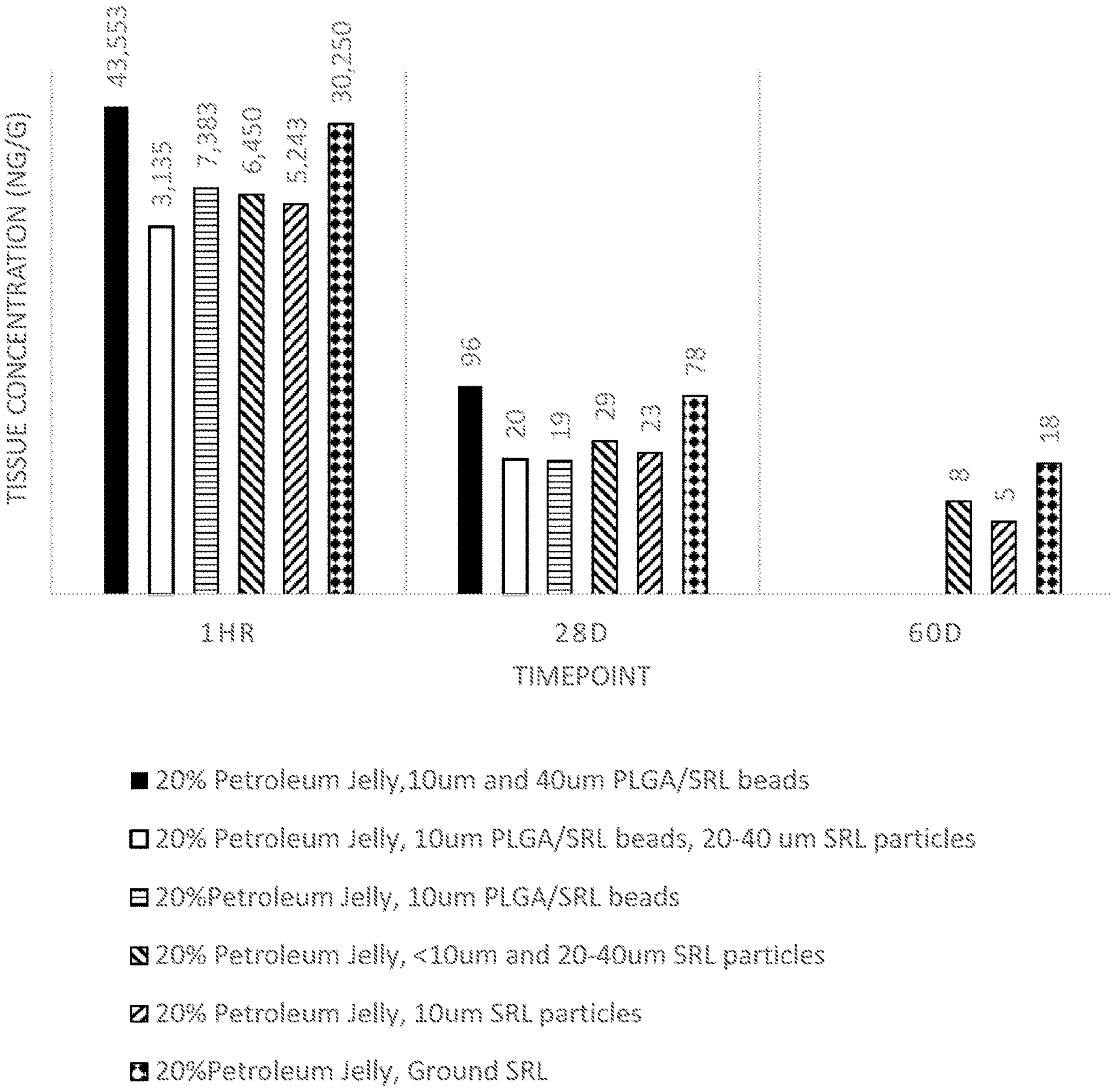
FIG. 6 depicts preclinical, arterial pharmacokinetic data from an animal study with a petroleum jelly excipient and comparing various microparticle and crystal size combinations.

This animal study also evaluated a separate excipient (petroleum jelly) with a variety of polymer microparticle and crystalline microparticle size combinations. The data seems to suggest that larger size particles (microspheres or crystals) lead to increased arterial drug levels (FIG. 6). It is important to note however that the collected data of the pharmacokinetics (PK) measure the total drug present which can include bioactive drug that has been taken up in the arterial tissue and also drug that is not bioactive, such as drug that remains encapsulated in polymer microparticles on the surface of the artery.

Example 3. Sirolimus/PLGA/Antioxidant (PLGA-DCM) Microparticle Fabrication with Microfluidics Sirolimus, PLGA and BHT were weighed and dissolved in dichloromethane (DCM) as a dispersing phase (2% to 5% solid). Polyvinyl alcohol (PVA) was weighed and dissolved into water as a continuous phase. The dispersing phase and continuous phase were pumped through a microfluidic chip of a microfluidic system from the Dolomite Microfluidics (Royston, UK) to form sirolimus, PLGA and dichloromethane droplets. Droplets were collected in PVA aqueous solution. After DCM was evaporated, sirolimus/PLGA microparticles were formed and collected either by filtration or centrifuge. Microparticle size and size distribution depends on dispersing phase flow rate, continuous phase flow rate, microfluidic chip channel size, solid percentage in the dispersing phase.

Example 4. Sirolimus/PLGA/Antioxidant (PLGA-EtOAc) Microparticle Fabrication with Membrane Emulsification Sirolimus, PLGA and BHT were weighed and dissolved in ethyl acetate as a dispersing phase (2% to 5%). Polyvinyl alcohol (PVA) was weighed and dissolved into water as a continuous phase (0.2% to 4%). The dispersing phase were pumped by a syringe pump through a membrane with many pores from a membrane emulsification system from Micropore Technologies Ltd (Redcar, UK) into a continuous phase reservoir. A mechanical stir inside the continuous phase reservoir sheared the dispersing phase off the membrane and formed sirolimus, PLGA and ethyl acetate droplets. Droplets were later transferred into bigger PVA aqueous solution reservoir. After ethyl acetate was evaporated, sirolimus/PLGA microparticles were formed and collected either by filtration or centrifuge. Microparticle size and size distribution depends on dispersing phase injection rate, stirring rate in the continuous phase reservoir, membrane pore size, and solid percentage in the dispersing phase.

Example 5. Crystalline Sirolimus Microparticle Fabrication with Ball Mill

Sirolimus as received is in crystalline form. One gram of crystalline sirolimus and some stainless-steel balls was added in a 5 ml grinding cup, and then ground with a Retsch MM400 ball mill at 30 Hz for 15 minutes. Crystallinity of the ground sirolimus was verified by DSC analysis. Particle size depends on frequency, time, and stainless-steel ball size. For smaller particle size wet grinding should be used.

Example 6. Preparation of Formulation 1

Crystalline sirolimus microparticles (less than 10 μm) from example 5, crystalline sirolimus particles (between 201 μm and 401 μm) from example 3, Lecithin, Suppocire BML, and sodium docusate were added into cyclohexane. After stirring and sonication, a drug coating suspension was made. The suspension was applied to the balloon surface of an angioplasty balloon catheter. The drug coating, Formulation 1, contains 24% (w/w) crystalline sirolimus dispersed in 60% (w/w) of Suppocire BML, 12% (w/w) of lecithin and 5% (w/w) of sodium docusate.

Example 7. Preparation of Formulation 2

Crystalline sirolimus microparticles (less than 10 μm) from example 5, crystalline sirolimus particles (between 20 μm and 40 μm) from example 5, Petroleum jelly, and lecithin were added into cyclohexane. After stirring and sonication, a drug coating suspension was made. The suspension was applied to the balloon surface of an angioplasty balloon catheter. The drug coating, Formulation 2, contains 80% (w/w) crystalline sirolimus dispersed in 17% (w/w) of petroleum jelly and 3% (w/w) of lecithin.

Example 8. Preparation of Formulation 3

Crystalline sirolimus microparticles (less than 10 μm) from example 5, crystalline sirolimus particles (between 20 μm and 40 μm) from example 5 and sodium docusate were added into cyclohexane. After stirring and sonication, a drug coating suspension was made. The suspension was applied to the balloon surface of an angioplasty balloon catheter. The drug coating, Formulation 3, contains 50% (w/w) crystalline sirolimus dispersed in 50% (w/w) of sodium docusate.

Example 9. Preparation of Formulation 4

Crystalline sirolimus microparticles (less than 10 μm) from example 5, crystalline sirolimus particles (between 20 μm and 40 μm) from example 5, Lecithin, Suppocire BML, and sodium docusate were added into cyclohexane. After stirring and sonication, a drug coating suspension was made. The suspension was applied to the balloon surface of an angioplasty balloon catheter. The drug coating, Formulation 4, contains 72% (w/w) crystalline sirolimus dispersed in 22% (w/w) of Suppocire BML, 4% (w/w) of lecithin and 2% (w/w) of sodium docusate.

Example 10. Preparation of Formulation 5

Crystalline sirolimus microparticles (less than 10 μm), Petroleum jelly, and lecithin were added into cyclohexane. After stirring and sonication, a drug coating suspension was made. The suspension was applied to the balloon surface of an angioplasty balloon catheter. The drug coating, Formulation 5, contains 81% (w/w) crystalline sirolimus dispersed in 16% (w/w) of petroleum jelly and 3% (w/w) of lecithin.

Example 11. Preparation of Formulation 6

Crystalline sirolimus microparticles from example 5, Petroleum jelly, and lecithin were added into cyclohexane. After stirring and sonication, a drug coating suspension was made. The suspension was applied to the balloon surface of an angioplasty balloon catheter. The drug coating, Formulation 6, contains 81% (w/w) crystalline sirolimus dispersed in 16% (w/w) of petroleum jelly and 3% (w/w) of lecithin.

Example 12. Preparation of Formulation 7

Sirolimus/PLGA microparticles from Example 3 (~10 μm), Sirolimus/PLGA microparticles from Example 3 (~35 μm), Lecithin, Suppocire BML, and sodium docusate were added into cyclohexane. After stirring and sonication, a drug coating suspension was made. The suspension was applied to the balloon surface of an angioplasty balloon catheter. The drug coating, Formulation 7, contains 17.6% (w/w) sirolimus dispersed in 26.4% (w/w) of PLGA, 44% (w/w) of Suppocire BML, 9% (w/w) of lecithin and 4% (w/w) of sodium docusate.

Example 13. Preparation of Formulation 8

Sirolimus/PLGA microparticles from Example 3 (~10 μm), Sirolimus/PLGA microparticles from Example 3 (~35 μm), Petroleum jelly, and lecithin were added into cyclohexane. After stirring and sonication, a drug coating suspension was made. The suspension was applied to the balloon surface of an angioplasty balloon catheter. The drug coating, Formulation 8, contains 36.8% (w/w) sirolimus dispersed in 55.2% (w/w) of PLGA, 7% (w/w) of petroleum jelly and 1% (w/w) of lecithin.

Example 14. Preparation of Formulation 9

Sirolimus/PLGA microparticles from Example 3 (~10 μm), Sirolimus/PLGA microparticles from Example 3 (~35 μm), and sodium docusate were added into cyclohexane. After stirring and sonication, a drug coating suspension was made. The suspension was applied to the balloon surface of an angioplasty balloon catheter. The drug coating, Formulation 9, contains 28.4% (w/w) sirolimus dispersed in 42.6% (w/w) of PLGA and 29% (w/w) of sodium docusate.

Example 15. Preparation of Formulation 10

Sirolimus/PLGA microparticles from Example 3 (~10 μm), crystalline sirolimus particles (between 201 μm and 401 μm) from example 5, Petroleum jelly, and lecithin were added into cyclohexane. After stirring and sonication, a drug coating suspension was made. The suspension was applied to the balloon surface of an angioplasty balloon catheter. The drug coating, Formulation 10, contains 50% (w/w) sirolimus dispersed in 28% (w/w) of PLGA, 10% (w/w) of petroleum jelly and 2% (w/w) of lecithin.

Example 16. Preparation of Formulation 11

Sirolimus/PLGA microparticles from Example 3 (~10 μm), Petroleum jelly, and lecithin were added into cyclohexane. After stirring and sonication, a drug coating suspension was made. The suspension was applied to the balloon surface of an angioplasty balloon catheter. The drug coating, Formulation 11, contains 36.4% (w/w) sirolimus dispersed in 54.6% (w/w) of PLGA, 7% (w/w) of petroleum jelly and 1% (w/w) of lecithin.

Example 17. Preparation of Formulation 12

Sirolimus/PLGA microparticles from Example 4 (~10 μm), Sirolimus/PLGA microparticles from Example 4 (~35 μm), and sodium docusate were added into cyclohexane. After stirring and sonication, a drug coating suspension was made. The suspension was applied to the balloon surface of an angioplasty balloon catheter. The drug coating, Formulation 12, contains 28.4% (w/w) sirolimus dispersed in 42.6% (w/w) of PLGA and 29% (w/w) of sodium docusate.

Example 18. PK Study in Peripheral Artery Porcine Model 5.0 mm×40 mm and 4×40 mm PSC2 PTA balloon catheters (ClearStream) were coated with Formulations 1 to 11 at 3.0 μg/mm$^2$. After, each coated balloon was folded and packaged in a sterilization pouch, it was sterilized with EtO (ethylene oxide). Testing devices along with a control device, MagicTouch DCB (Concept Medical, Tampa FL), were tested in a domestic swine femoral artery model at 1 hour, 28 days and 60 days with a sample size of 4 at each time point. Each animal received up to four drug coated balloon treatments, one in each target artery. The targeted sites (anatomy permitting) are as follows: left internal femoral (LIF), left external femoral (LEF), right internal femoral (RIF), and right external femoral (REF). If the size of femoral arteries was not in target size range, external iliac arteries with proper size were used. Target treatment site was measured by quantitative vascular angiography. Proper balloon size and inflation pressure were selected to achieve target overstretch ratio 20% to 30%. Drug coated balloon was delivered to the target site, inflated to the target pressure and maintained at the pressure for 2 minutes. Used balloon was collected after balloon was deflated and withdrawn out of the body. Animals were humanely euthanized at their designated termination time points and subjected to a limited necropsy. Treated vessels were harvested for Sirolimus content and concentration analysis. PK results are listed in the following Table 2.

TABLE 2

| | Sirolimus level in arterial tissue (ng/g) | | |
|---|---|---|---|
| Formulations | 1 hour | 28 d | 60 d |
| Formulation 1 | 34,225 | 98 | 45 |
| Formulation 2 | 6,450 | 29 | 8 |
| Formulation 3 | 171,250 | 100 | 53 |
| Formulation 4 | 5,243 | 23 | 6 |
| Formulation 5 | 9,708 | 57 | 6 |
| Formulation 6 | 30,250 | 78 | 26 |
| Formulation 7 | 117,238 | 41 | 46 |
| Formulation 8 | 43,553 | 96 | 47 |
| Formulation 9 | 280,698 | 2,784 | 5,068 |
| Formulation 10 | 3,135 | 20 | 20 |
| Formulation 11 | 7,383 | 19 | 19 |
| MagicTouch DCB | 3,910 | 25 | 14 |

Example 19. PK Study in Peripheral Artery Porcine Model 5.0 mm×40 mm and 4×40 mm PSC2 PTA balloon catheters (ClearStream) were coated with Formulations 9 and 12 at 3.0 pig/mm$^2$. After the coated balloon was folded and packaged in a sterilization pouch, it was sterilized with EtO. Testing devices were tested in a domestic swine femoral artery model at 1 hour, 7 days, 28 days, 60 days, and 90 days with a sample size of 6 at each time point. Each animal received up to four drug coated balloon treatments, one in each target artery. The targeted sites (anatomy permitting) are as follows: LIF, LEF, RIF, and REF. If the size of femoral arteries was not in target size range, external iliac arteries with proper size were used. Target treatment site was measured by quantitative vascular angiography. Proper balloon size and inflation pressure were selected to achieve target overstretch ratio 20% to 30%. Drug coated balloon was delivered to the target site, inflated to the target pressure and maintained at the pressure for 2 minutes. Used balloon was collected after balloon was deflated and withdrawn out of the body. Animals were humanely euthanized at their designated termination time points and subjected to a limited necropsy. Treated vessels were harvested for Sirolimus content and concentration analysis. PK results are listed in the following Table 3.

TABLE 3

| | Sirolimus (SRL) in Arterial Tissue (ng/g) | | | | |
|---|---|---|---|---|---|
| | 1 hr | 7 d | 28 d | 60 d | 90 d |
| Formulation 9 | 41583 | 3804 | 1996 | 1287 | 212 |
| Formulation 12 | 1355 | 281 | 154 | 329 | 701 |

Example 20: Slurry Coating by Pipette

A two-stop pipette was utilized to coat a slurry on the surface of a balloon. The slurry was of 10 and 40 μm sirolimus polymer microparticles with 250 mg of sodium docusate in an amber vial in 10 mL of cyclohexane. A PTFE coated stir bar was used and the vial was swirled to ensure the bar could contact the walls of the vial. Immediately prior to taking a dispense, the vial was gently swirled 2-3 times, tilting as needed. For the 2-stop pipette, the 1$^{st}$ stop when depressing the plunger is used to dispense the volume selected and the 2$^{nd}$ stop when depressing the plunger: is used to expel all of the liquid from the tip. The pipette plunger was pressed to the 1$^{st}$ stop and held, then placed into the slurry solution, approximately right above the stir bar. The plunger was slowly released all the way to withdraw solution with the tip remaining in the slurry solution. Once the plunger was fully released, the pipette tip was removed from solution but not out of the vial. The plunger was then pressed to the 2$^{nd}$ stop to expel all of the liquid from the tip and then again to expel all liquid. The pipette was then pressed to the first stop and placed back in the slurry solution, when the plunger was slowly released to draw in the slurry. After the plunger was fully released, the tip was removed from the solution and the vial capped to avoid evaporation. The tip was held at the marker of the proximal end of the balloon and at a 45° angle in line with the balloon. The plunger was slowly depressed and the tip moved along toward the distal marker band of the balloon in a single pass without moving back to the proximal end or using the tip to spread the applied slurry solution. Once the distal end was reached, the plunger was pressed to the 2$^{nd}$ stop to expel all the liquid. The tip was then discarded.

From this process, it was then tested the location for withdrawal from the vial, the number of rinses, the changing of the tip, the technique for withdrawal, the type of tip and the solution aliquoting and real-time assay.

Figure 7A:
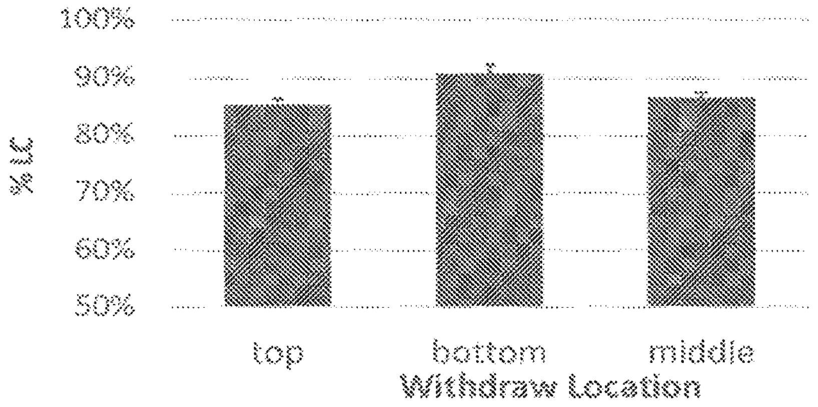
FIG. 7A shows the effect % coating of location within a container (top, middle, bottom)

For the withdrawal location, 5 samples of 50 uL each were taken for each condition. The "label claim" (% LC) amount of sirolimus for 50 uL dispenses is 1250 ug. FIG. 7A shows the seen results. All locations had small variation of approximately +/−3% RSD; however, the bottom pull location (defined as directly above the stir bar) was closest to the intended dosage. It was concluded that this would be the reference point used for the withdrawing location.

Figure 7B:
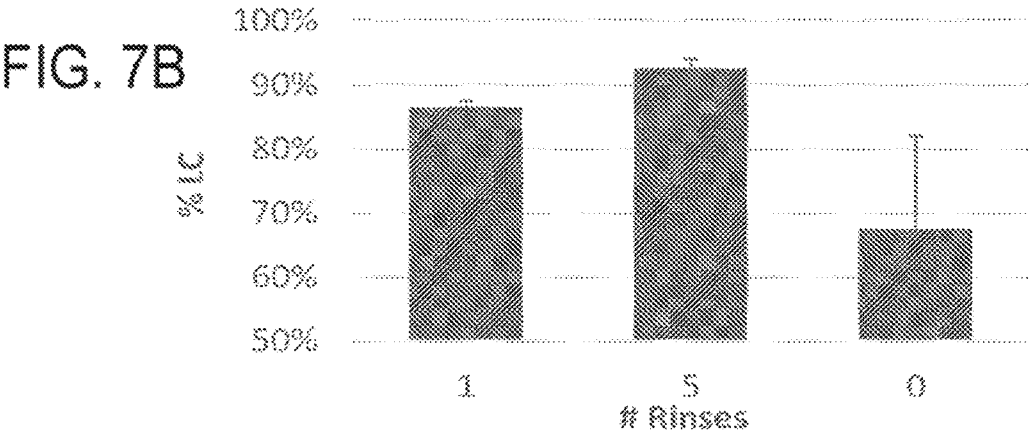
FIG. 7B shows the effects seen with how many times the pipette tip is rinsed prior to application of the slurry to the balloon.

For the number of pre-rinses or priming, proper pipette technique involves priming or "rinsing" the pipette tip before withdrawing solution to coat the tip with the liquid to increase volume accuracy. To rinse the tip, the set volume of liquid is withdrawn and then ejected back into the solution. The risk of rinsing the tip for a slurry is that the suspended particles may adhere to the tip resulting in a variance in accuracy. 5 samples of 50 uL each were taken for tests where the number of rinses was varied. FIG. 7B shows the results. The single- and five-time rinse dispenses were very consistent with a low % RSD; however, not rinsing the tip both dramatically decreased the amount of sirolimus dispensed as well as increased the % RSD. It was concluded that to optimize the consistency of drug dispensed and processing time and complexity, the pipette tip would be rinsed once prior to coating.

Figure 7C:
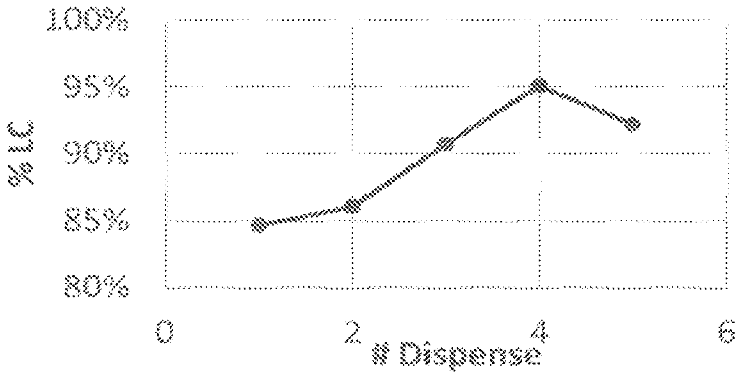
FIG. 7C shows the effects in coating seen when the tip of the pipette is not changed.
Figure 7D:
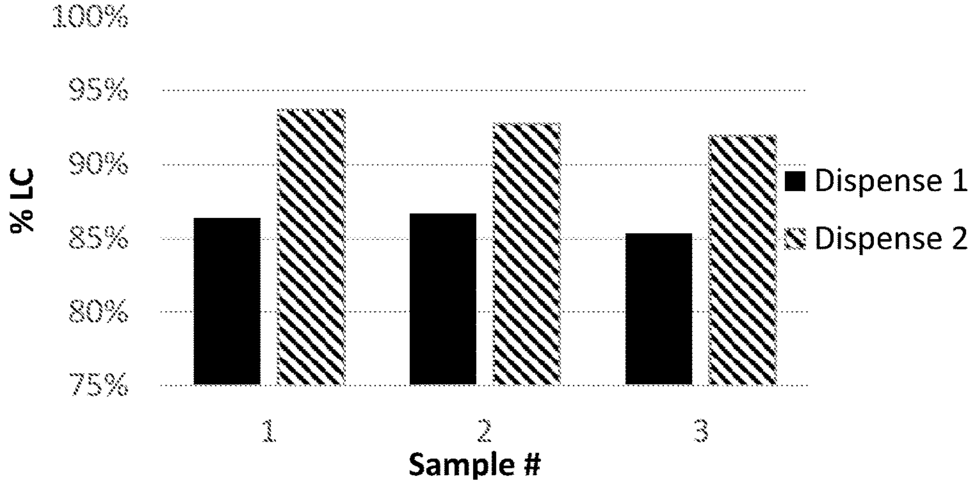
FIG. 7D shows the difference in coating between using a tip once and a second time.

With regard to changing the pipette tip, 50 μL of solution was dispensed 5 times in a row without changing the tip. The tip was rinsed before the first dispense. FIG. 7C shows the obtained results. The amount of sirolimus dispensed increased with more dispenses, likely due to particles adhering onto the pipette tip over time and being ejected during the subsequent dispense. 50 μL of solution was dispensed twice without changing the pipette tip to test if the increase in drug content between the first and second dispenses is consistent. FIG. 7D shows the results. The increase in sirolimus content was very consistent between the first and second dispenses, approximately 6-7%. The tips from this test were collected and tested for drug content, as well as other tips that were simply dipped in the coating solution without withdrawing and dispensing solution. Three tips were used for each test. The amount of sirolimus adhered to the pipette tips consistently increased with more dispenses, which aligned with results shown 7D. To optimize drug dosage consistency, it was concluded that the pipette tip would be discarded after each dispense to avoid the risk of additional sirolimus being dispensed after reusing the tip.

Figure 7E:
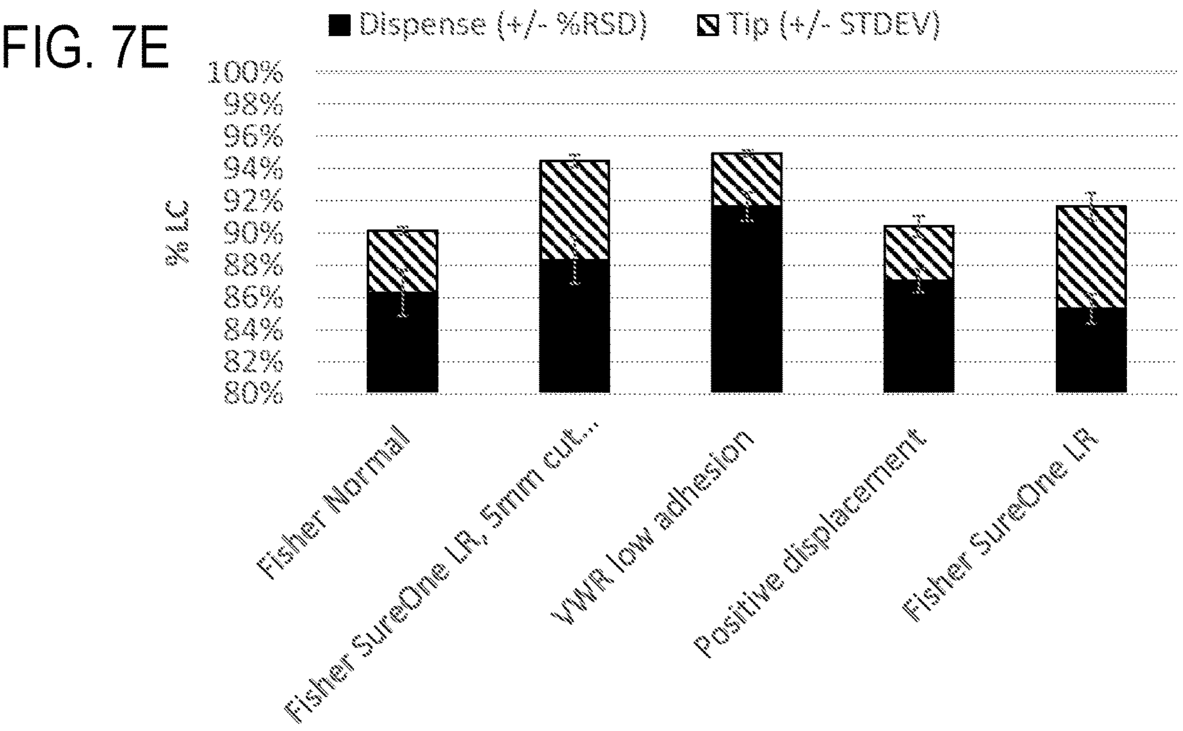
FIG. 7E shows the differences seen in coating with varying types of pipette tip. 7F shows the effects of coating based on pipette technique.

With respect to the type of pipette tip utilized, FIG. 7E shows results obtained using various brands and materials as identified therein. All pipette tips were consistent; however, the Fisher low retention with 5 mm cut off and VWR low adhesion tips had the highest drug content dispensed. 5 mm of the Fisher low retention tip was cut off to prevent the particles from clogging the tip.

Figure 7F:
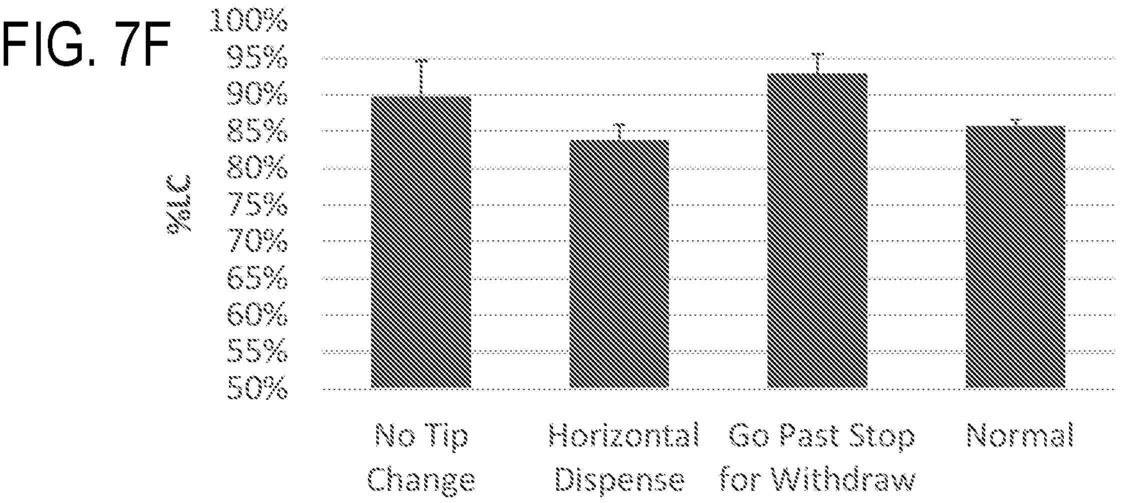
FIG. 7 depicts the effects of variance in pipetting a slurry solution of microparticle on the surface of a balloon.
FIG. 7G shows the mL lost in different sized vials by leaving the slurry open to the atmosphere.
FIG. 7H shows the effects on coating from the identified aliquot concentrations.

The technique for withdrawing the slurry and dispensing the slurry was next assessed. Five 50 uL dispenses were taken for each condition, and the pipette tip was rinsed prior to the first dispense. The following conditions were tested: Normal technique, no tip change—withdraw from bottom of solution, rinse once, dispense in the vertical position; Horizontal dispense—withdraw solution normally, dispense with the pipette positioned horizontally; Go past stop for withdraw—rinse once, then push the plunger past the first stop to withdraw more solution than intended to be dispensed, and only dispense the set amount of solution; and, Normal technique—withdraw from bottom of solution, rinse once, dispense in the vertical position. FIG. 7F shows the results obtained. All techniques had a low % RSD except not changing the tip. Although technique 'c' (go past stop for withdraw) had the highest sirolimus dispensed, it was ruled out for use due to increased complexity. Based on these results, it was concluded that a normal technique and discarding the tip after each dispense was the easiest technique which gave very consistent dispensing results.

Figure 7G:
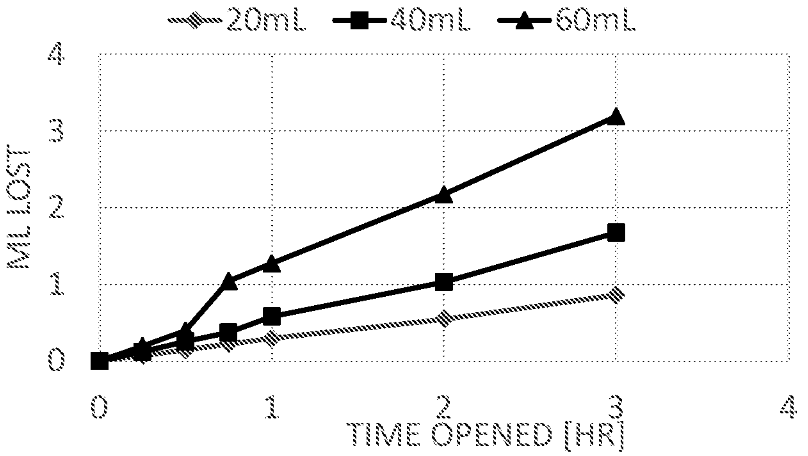
Figure 7H:
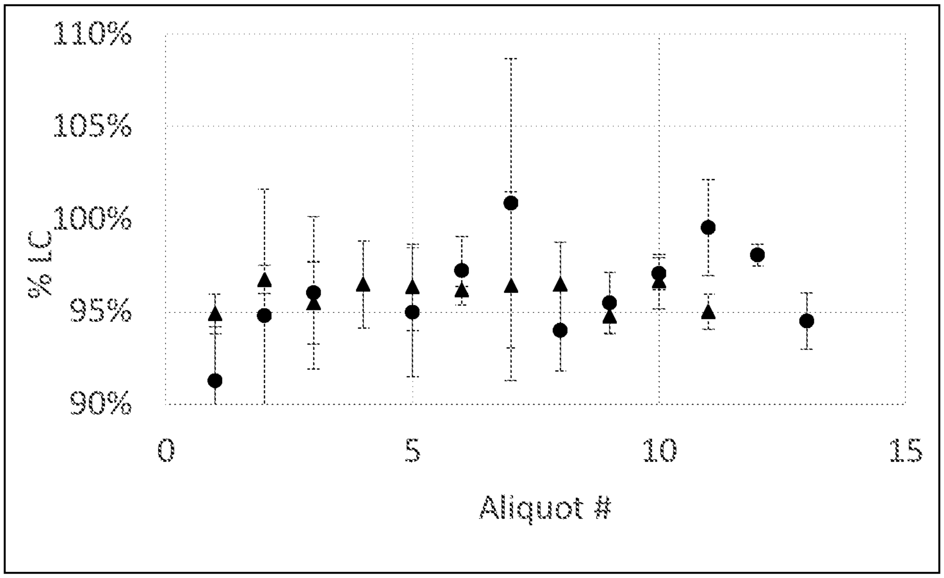

The pipette coating process is susceptible to an increase in drug concentration in the solution over time, as the volatile solvent (cyclohexane) evaporates as the user continuously removes the cap of the vial to withdraw solution. This loss of solvent over time was measured and is depicted in FIG. 7G. This phenomenon was observed during prolonged periods of coating balloon catheters. During coating, one in-process assay sample was taken every 20 balloons coated, where coating 20 balloons takes approximately 40 minutes to coat. The total coating time was approximately 4 hours, and the solution was capped during setup, breaks, and shut down. The solution concentration steadily increased as the solvent evaporated, starting at 92% LC and increasing to 117% LC by the end of the day. One solution to evaporation is to take a solution sample after coating 20 balloons, wait for the results, and then adjust the dispense volume based on the solution concentration. For example, an initial dispense was taken (72 uL), the dispense volume was reduced to 64 uL since the concentration was too high, then 20 parts were coated, another sample was taken revealing another increase in solution concentration, the dispense volume was reduced to 58 uL, and so on. The second method to address evaporation is to make one large solution and split it into smaller aliquots, where each aliquot would be used to coat only 20 parts. Here, the analytical results are obtained prior to beginning manufacturing, so there is no downtime during coating to wait for results. An 85 mL 'master' solution was made, and after all the particles were sufficiently stirred and suspended, 7.5 mL was transferred to an aliquot (smaller vial) also containing a stir bar. This was repeated 13 times for 13 aliquots total. After transferring each 7.5 mL, three 50 uL samples were taken from the master solution to check if the concentration increased or decreased. Three 50 uL samples were also taken from each aliquot to check their concentration. FIG. 7H shows the results. The master solution and aliquot concentration were very similar, and all aliquot concentrations were very consistent between 95-97% LC.

Example 21: Slurry Coating by Automation

Experiments were designed to asses the parameters for manufacturing using an "Autocoater" where the operator loads the catheter into the machine, and the coating is applied automatically using a syringe pump and a sophisticated automated system. To adapt for the slurry, a stirring syringe was utilized. Testing was performed with crystalline microparticles in a solvent solution with petrolatum and lecithin. The solvent was cyclohexane and a PTFE stirring bar was utilized in a stirring syringe by Sono-Tek that has a recess built into the plunger where the magnetic stir bar sits. The stir speed is then controlled by an external module, and the syringe may be loaded into standard pump to dispense solution. Three variables were tested with the stirring syringe—syringe orientation (45 degrees pointed down vs vertical pointing down), stir speed (low (1-300 rpm), medium (300-650 rpm), high (700-3000 rpm)), and dispense rate (fast vs slow) (3-100 μL/s). No tubing was connected to the syringe—the dispenses were collected directly from the outlet of the syringe.

Figure 8A:
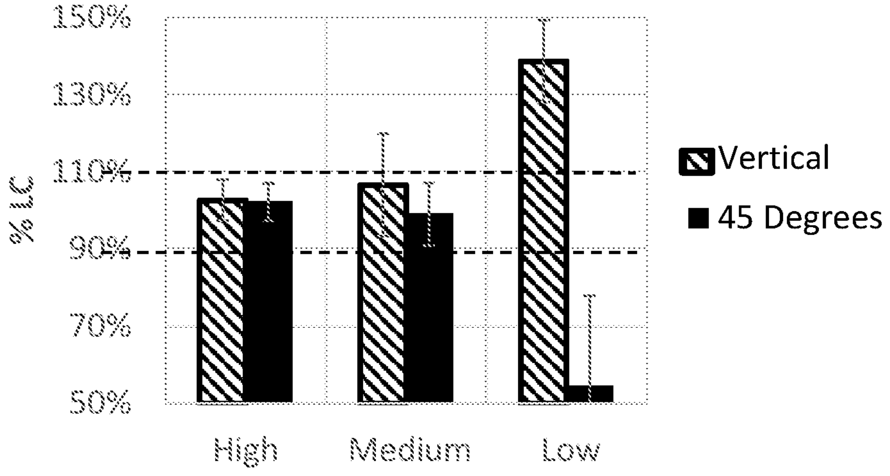
FIG. 8A shows the effects of stir speed and syringe orientation of coating.
Figure 8B:
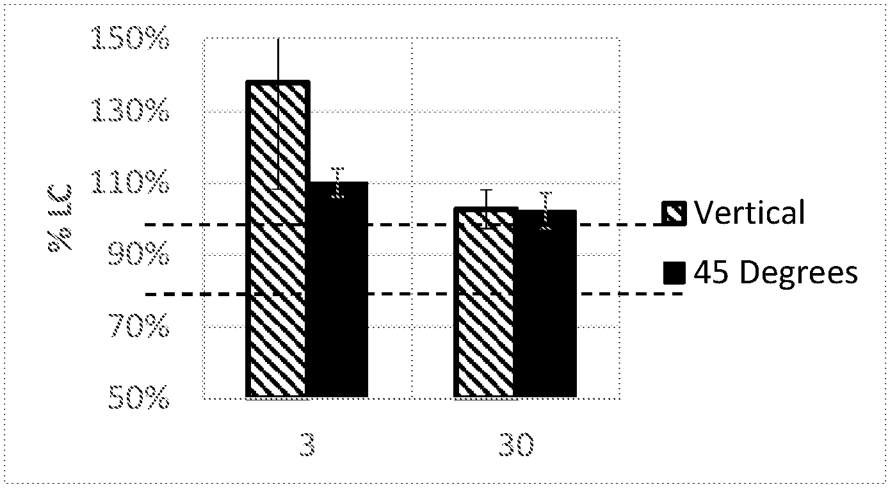
FIG. 8B shows the effects from orientation of dispensing and the dispense rate.

FIG. 8A shows the results from stir speed and syringe orientation. The high and medium stir speeds were relatively consistent and were not affected by syringe orientation. However, at a low stir speed the drug content increased because all the particles settled at the syringe opening, and at 45 degrees they settled in the corner of the syringe away from the syringe opening. FIG. 8B shows results in orientation and dispensing rate. A faster dispense rate produced much more consistent results. This could be due to the accuracy capabilities of the syringe and pump combination.

Figure 8C:
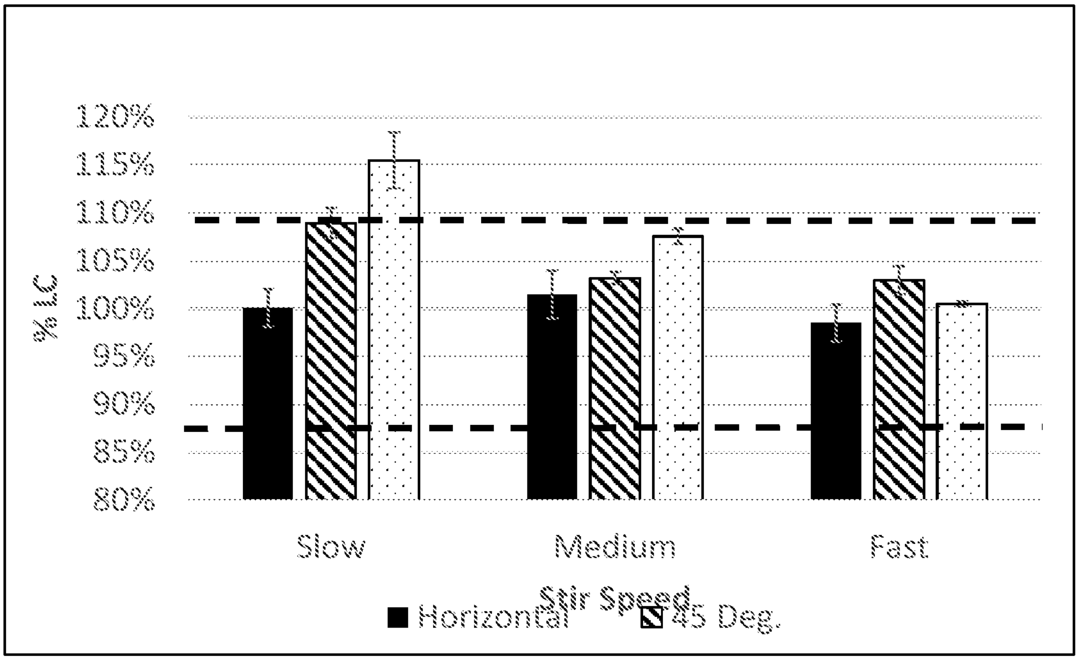
FIG. 8C shows the effect with a second automated machine with orientation and stirring speed.
Figure 8D:
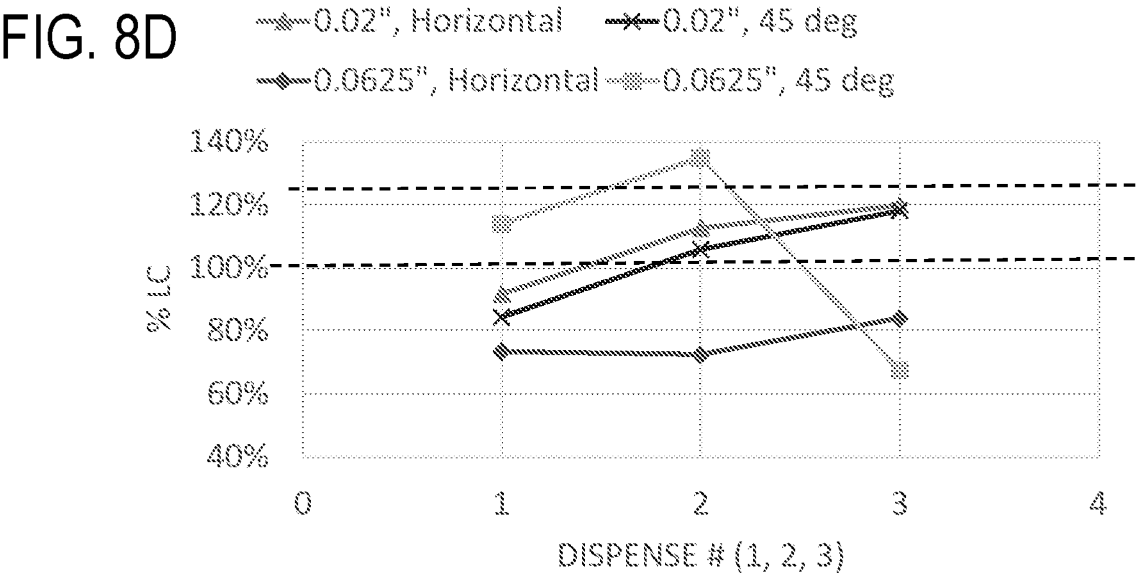
FIG. 8D shows the effects seen in coating with changes to the tubing size and the orientation of the syringe.

As the Sono-Tek syringe has volume limitation, a neMIX from Cetoni was tested as well that includes a stirring module that both rotates the stir bar and moves back and forth linearly to mix the solution. Syringe volume, stir bar size, pump orientation, stir speed, and linear speed were tested. A dispense tip approximately 1" long was connected to the outlet of a 50 mL syringe. FIG. 8C shows the results seen with identified orientation and stir speeds. The faster stir speed decreased variability in dispenses. In this system, orientation does not seem to affect dispense consistency, but the vertical pointed downward position was the most consistent. The % RSD for all the tests was very low, showing that the stirring capabilities are sufficient for the microparticle coating processes. The issue with using a syringe pump to dispense a slurry is that the dispense tip must be connected directly to the end of the syringe. Otherwise, any tubing between the syringe and dispense tip can cause settling of the suspended particles which would affect the dose consistency. To test this, a syringe with various tubing sizes was used to withdraw solution similar to the pipette method, and the syringe pump was used to dispense the solution out of the tubing. FIG. 8D shows the results obtained. The results show that using any tubing is more variable and less accurate than using the pipette coating method or using a stirring syringe pump without any tubing. Both the large and small tubing sizes were affected by the orientation of the tubing, which would be difficult to control if a syringe pump was implemented in an Autocoater.

Aspects as described herein are directed the systems, methods, and catheters for endovascular treatment of a blood vessel. Endovascular treatments may include, but are not limited to, fistula formation, vessel occlusion, angioplasty, thrombectomy, atherectomy, crossing, drug coated balloon angioplasty, stenting (uncovered and covered), lytic therapy. Accordingly, while various aspects are directed to fistula formation between two blood vessels, other vascular treatments are contemplated and possible.

While particular aspects have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A formulation for a balloon of a balloon catheter, comprising:

a first group of polymer microparticles and a second group of polymer microparticles, each group comprising poly(lactic-co-glycolic acid) (PLGA) and a therapeutic agent loaded therein, wherein polymer microparticles of the first group of polymer microparticles have a smaller average size than polymer microparticles of the second group of polymer microparticles configured for an initial burst of the therapeutic agent and a sustained release of the therapeutic agent, respectively, and the therapeutic agent is a limus drug and is of 10 to 50% w/w; and an excipient, wherein the excipient is sodium docusate, petrolatum, or sodium docusate and petrolatum.

2. The formulation of claim 1, wherein the polymer microparticles are smooth with even distribution of the therapeutic agent.

3. The formulation of claim 1, wherein the polymer microparticles are contoured with clustered distribution of the therapeutic agent.

4. The formulation of claim 2, further comprising an antioxidant, wherein the antioxidant is butylated hydroxytoluene (BHT).

5. The formulation of claim 1, wherein the therapeutic agent is sirolimus.

6. The formulation of claim 1, wherein the therapeutic agent is sirolimus and sirolimus is loaded in the polymer microparticles at 40% w/w.

7. The formulation of claim 6, wherein the PLGA is of 75:25 of lactide to glycolide.

8. The formulation of claim 7, wherein the polymer microparticles of the second group of polymer microparticles is of an average size that is of 20 μm to 30 μm larger than the polymer microparticles of the first group of polymer microparticles.

9. The formulation of claim 8, wherein the polymer microparticles of the first group of polymer microparticles have an average size of 10 μm.

10. The formulation of claim 9, wherein the polymer microparticles of the second group of polymer microparticles have an average size of 30 μm.

11. The formulation of claim 9, wherein the polymer microparticles of the second group of polymer microparticles have an average size of 35 μm.

12. The formulation of claim 9, wherein the polymer microparticles of the second group of polymer microparticles have an average size of 40 μm.

13. A formulation for a balloon of a balloon catheter, comprising:

a first group of polymer microparticles and a second group of polymer microparticles, each group comprising poly(lactic-co-glycolic acid) (PLGA) and a therapeutic agent loaded therein, wherein polymer microparticles of the first group of polymer microparticles have a smaller average size than polymer microparticles of the second group of polymer microparticles configured for an initial burst of the therapeutic agent and a sustained release of the therapeutic agent, respectively, and the therapeutic agent is a limus drug and is of 10 to 50% w/w of the polymer microparticles; and an excipient, wherein the excipient is sodium docusate, petrolatum, or sodium docusate and petrolatum, wherein the polymer microparticles of the second group of polymer microparticles is of an average size that is 18-33 μm larger than the polymer microparticles of the first group of polymer microparticles.

14. The formulation of claim 13, wherein the polymer microparticles are smooth with an even distribution of the therapeutic agent therein.

15. The formulation of claim 13, wherein the polymer microparticles are contoured with a clustered distribution of the therapeutic agent therein.

16. The formulation of claim 14, further comprising an antioxidant, wherein the antioxidant is butylated hydroxytoluene (BHT).

17. The formulation of claim 16, wherein the therapeutic agent is sirolimus.

18. The formulation of claim 17, wherein sirolimus is loaded in the polymer microparticles at 40% w/w.

19. The formulation of claim 18, wherein the PLGA is of 75:25 of lactide to glycolide.

20. The formulation of claim 19, wherein the polymer microparticles of the first group of polymer microparticles have an average size of 10 μm.

21. The formulation of claim 19, wherein the polymer microparticles of the second group of polymer microparticles have an average size of 30 μm.

22. The formulation of claim 19, wherein the polymer microparticles of the second group of polymer microparticles have an average size of 35 μm.

23. The formulation of claim 19, wherein the polymer microparticles of the second group of polymer microparticles have an average size of 40 μm.

* * * * *